(12) United States Patent
Cobbs et al.

(10) Patent No.: US 8,716,257 B2
(45) Date of Patent: May 6, 2014

(54) CMV GENE PRODUCTS PROMOTE CANCER STEM CELL GROWTH

(75) Inventors: Charles Cobbs, San Francisco, CA (US); Liliana Soroceanu, San Francisco, CA (US)

(73) Assignee: Sutter West Bay Hospitals, San Francisco, CA (US)

( * ) Notice: Subject to any disclaimer, the term of this patent is extended or adjusted under 35 U.S.C. 154(b) by 0 days.

(21) Appl. No.: 13/447,249

(22) Filed: Apr. 15, 2012

(65) Prior Publication Data

US 2012/0264675 A1 Oct. 18, 2012

Related U.S. Application Data

(60) Provisional application No. 61/476,234, filed on Apr. 15, 2011.

(51) Int. Cl.
*C12N 15/11* (2006.01)
*C07H 21/04* (2006.01)

(52) U.S. Cl.
USPC ..................................... 514/44 A; 536/24.5

(58) Field of Classification Search
None
See application file for complete search history.

(56) References Cited

U.S. PATENT DOCUMENTS

| 2004/0082005 | A1 | 4/2004 | Cobbs |
| 2004/0229266 | A1* | 11/2004 | Tuschl et al. ..................... 435/6 |
| 2004/0248839 | A1* | 12/2004 | Kowalik ......................... 514/44 |
| 2011/0311523 | A1 | 12/2011 | Cobbs |

OTHER PUBLICATIONS

Cobbs et al (Cancer Research 62, 3347-3350, Jun. 15, 2002).*
Mitchell et al (Neuro-Oncology 10, 10-18, 2008).*
Lucas (J. Neurooncol. 103:231-238, published online Sep. 2010).*
Barami et al (J. Clin. Neurosci. 17: 819-823, 2010).*
Dziurzynski et al (Clin Cancer Res 17: 4642-4649, published online Apr. 13, 2011).*
Lee et al (GLIA 51:1-12, 2005).*
Su et al (Cancer Res 63:3585-3592, 2003).*
Plunkett et al (J Neurosurg 90:1072-1077, 1999).*
Pari et al (The Journal of Infectious Diseases 177:523-528, 1998).*
Straat et al (J Natl Cancer Inst101: 488-497, 2009).*
Zhao et al (Int. J, Oncol. 31: 361-368, 2007).*
Williams et al (Curr. Oncol. 16(1): 56-58, 2009).*

* cited by examiner

*Primary Examiner* — Richard Schnizer
(74) *Attorney, Agent, or Firm* — Joseph R. Baker, Jr.; Gavrilovich, Dodd & Lindsey LLP

(57) ABSTRACT

The disclosure relates generally to compositions and methods useful for inhibiting the infection and propagation of viral particles, particularly members of the Herpesviridae family, and more particularly to cytomegalovirus (CMV) and methods of treating diseases and disorders, including cell proliferative disorders, associated with CMV infection.

8 Claims, 26 Drawing Sheets

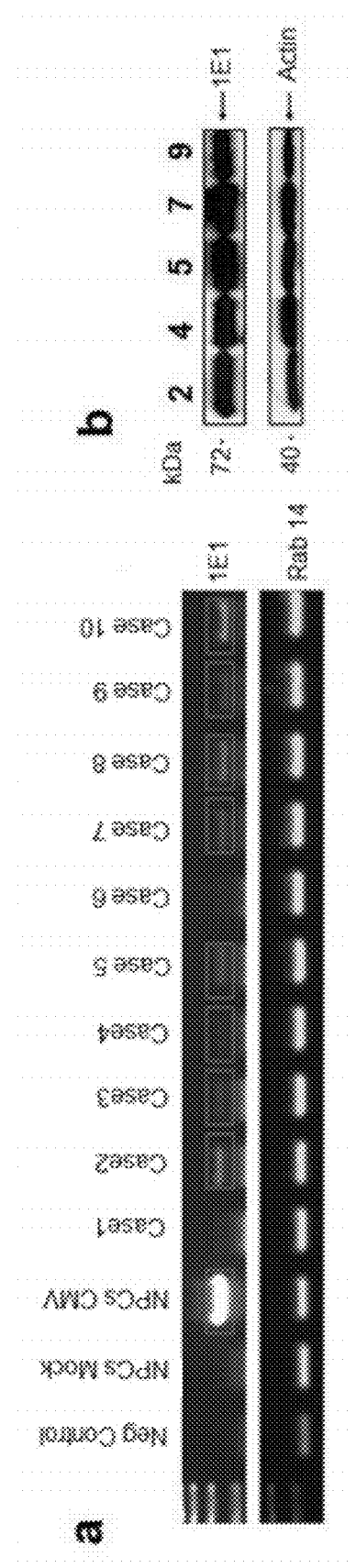
FIGURE 1A-B

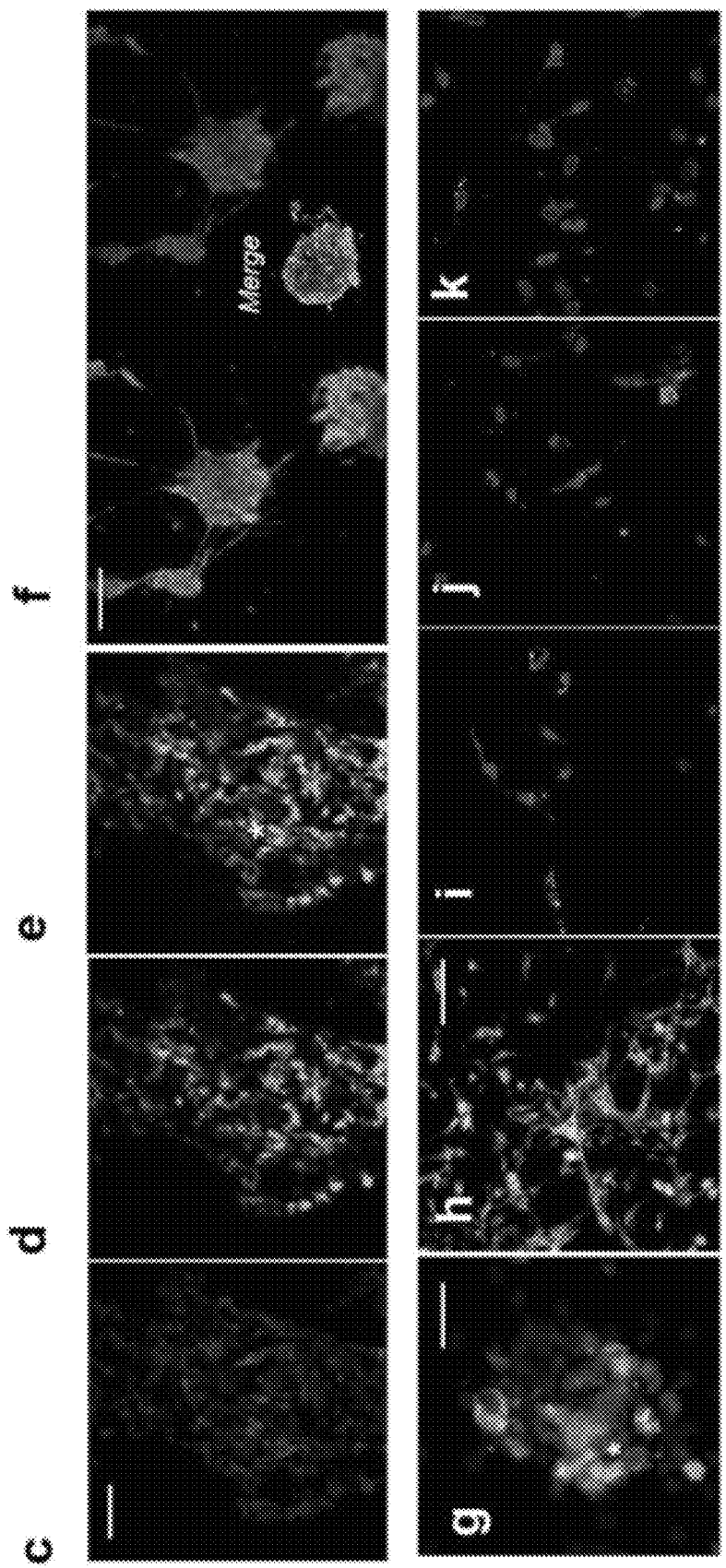
FIGURE 1C-K

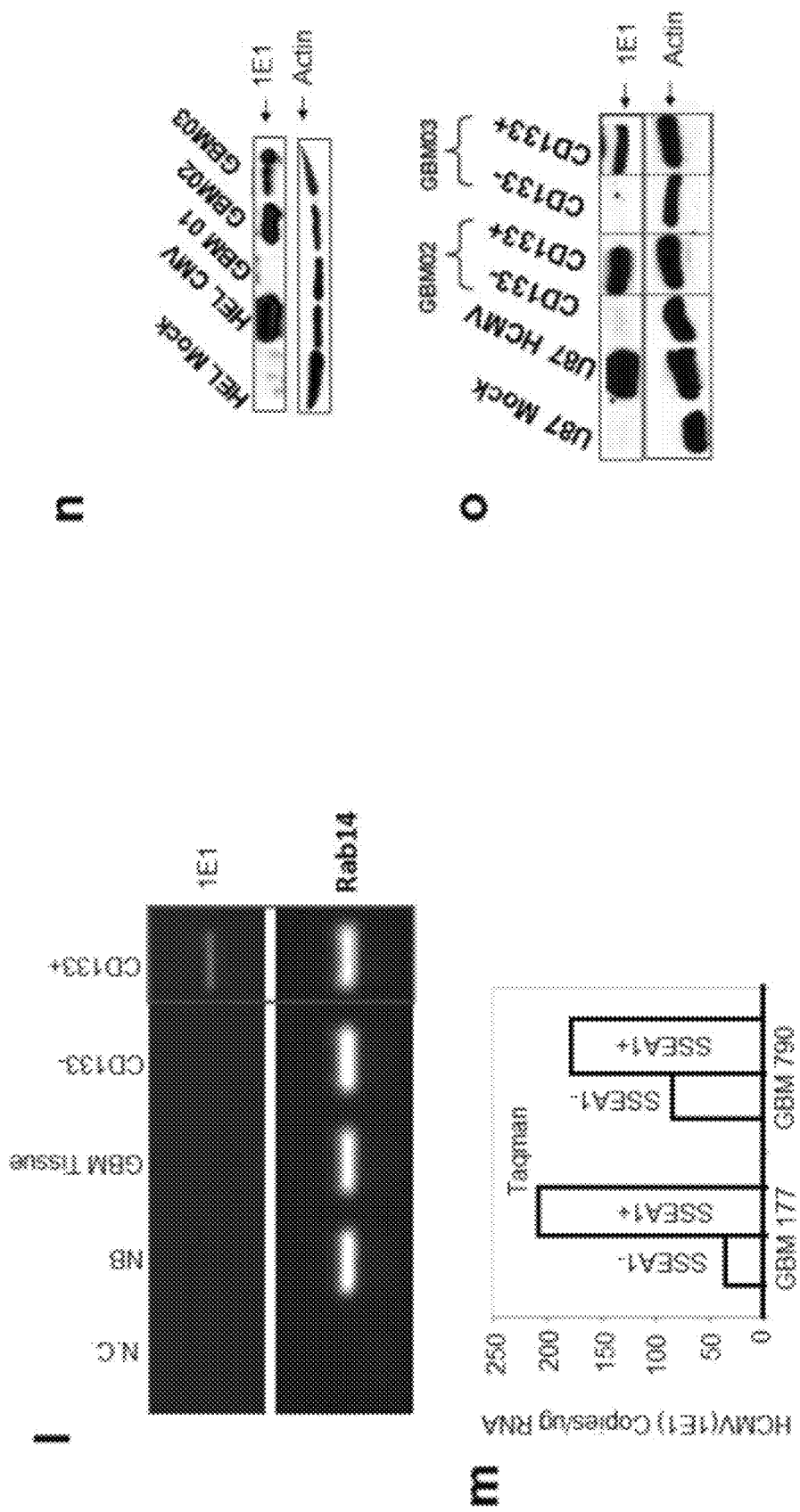
FIGURE 1L-O

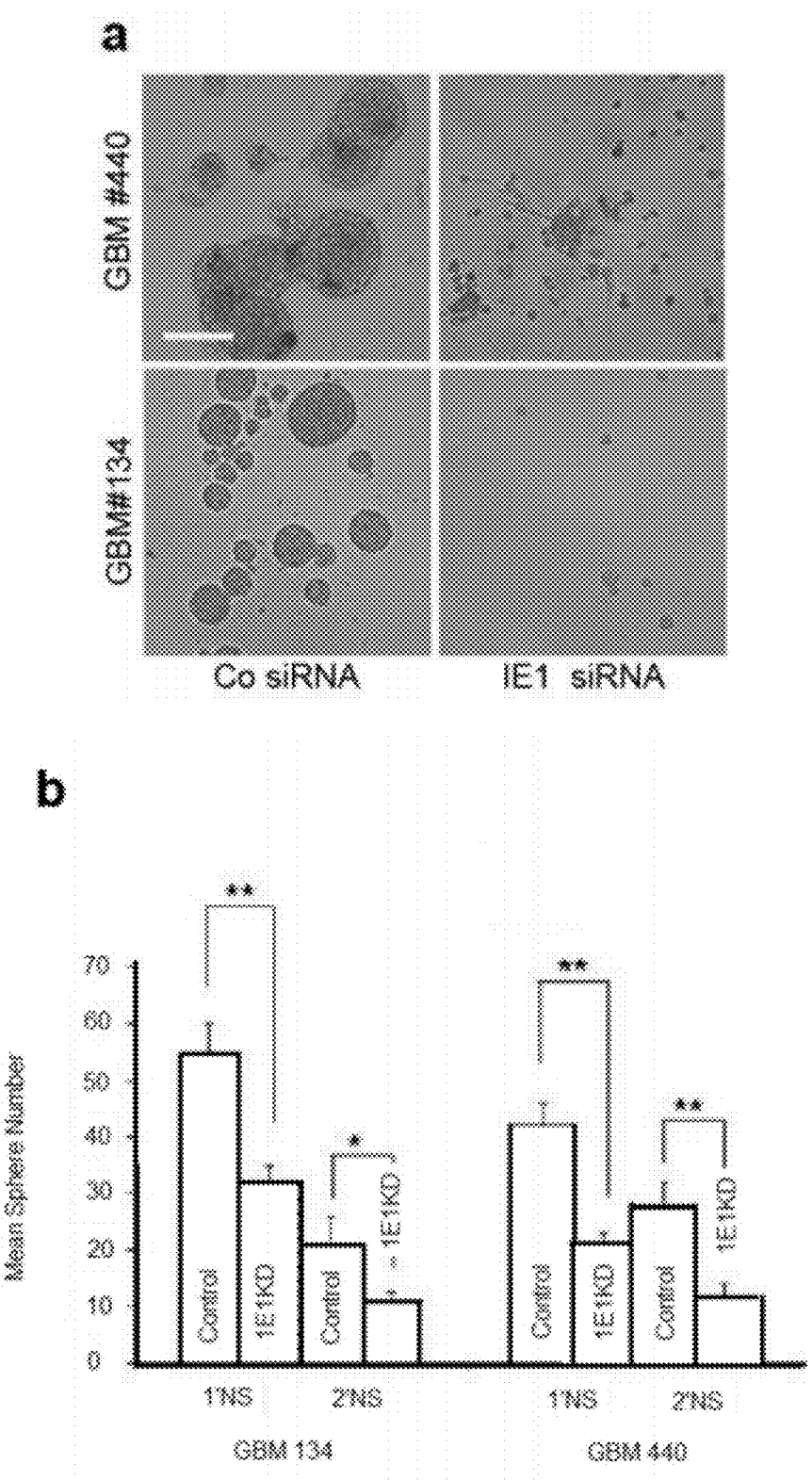
FIGURE 2A-B

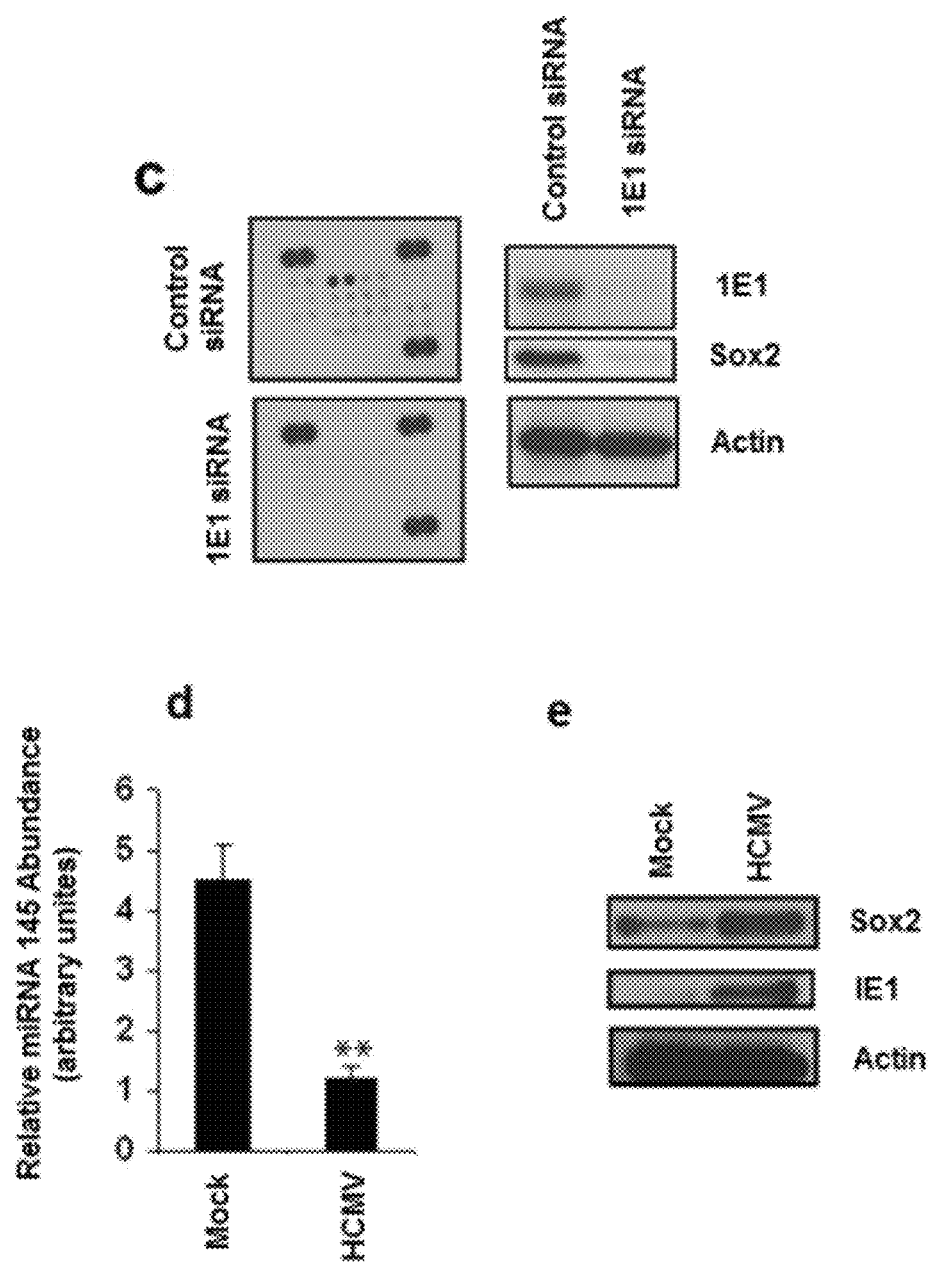
FIGURE 2C-E

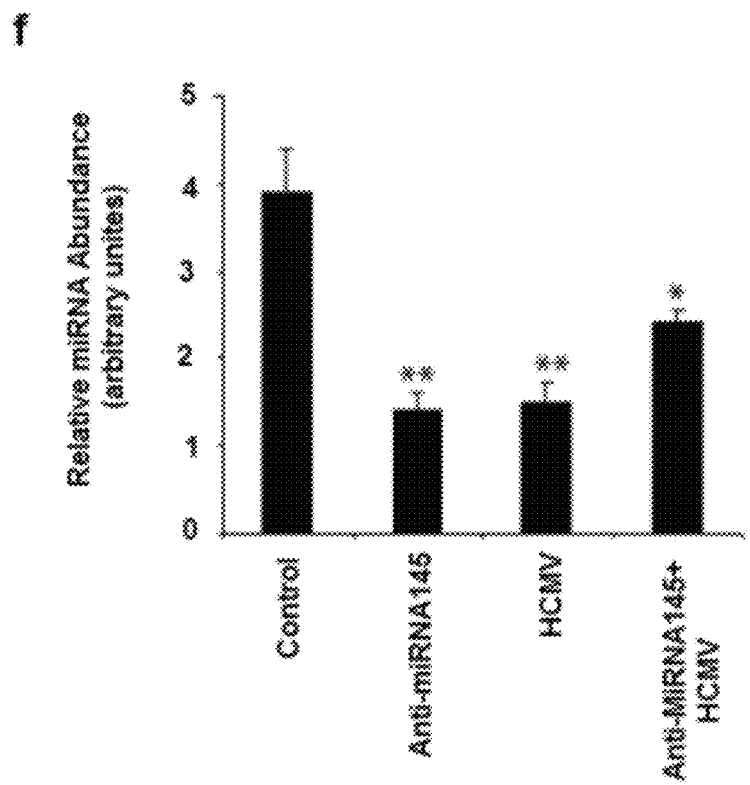
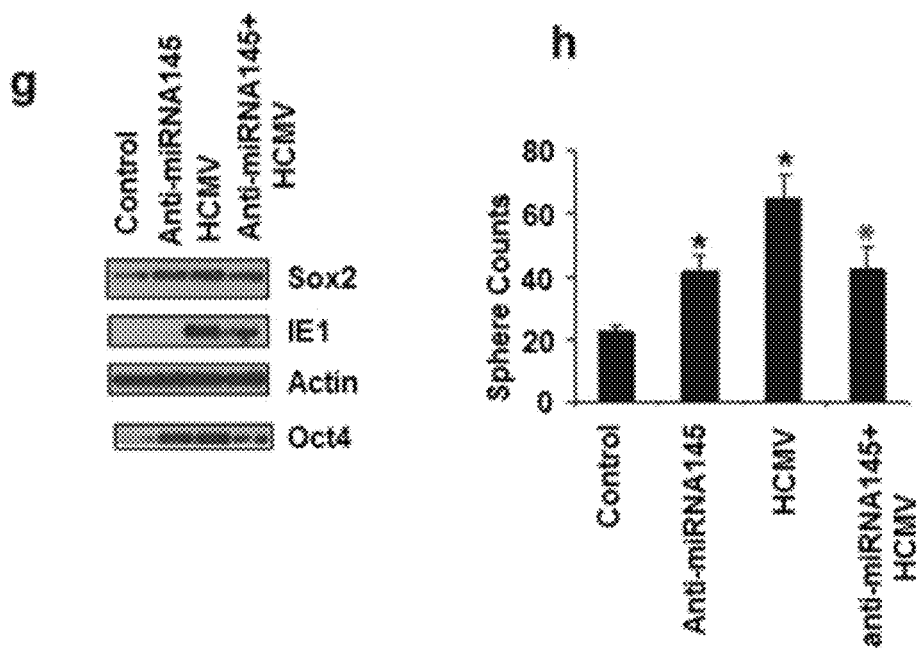
FIGURE 2F-H

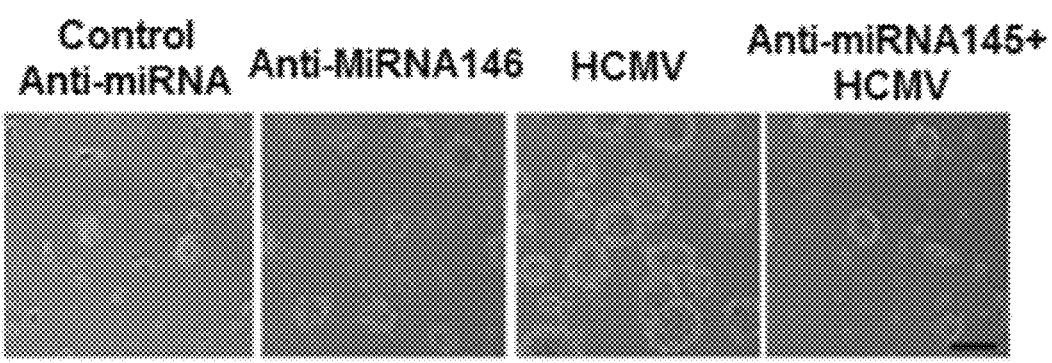
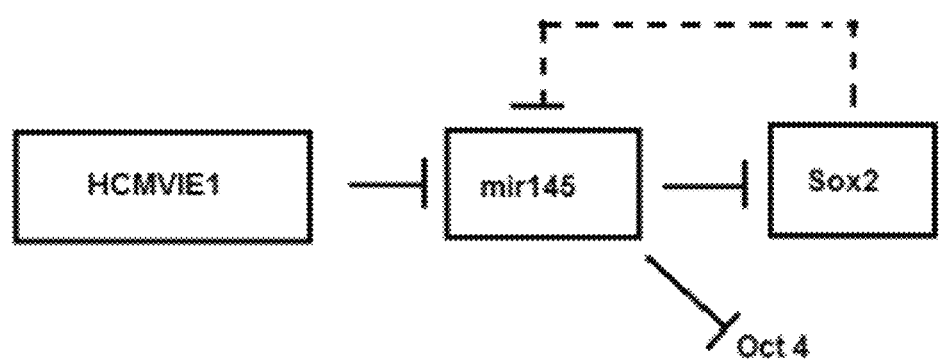
FIGURE 2I-J

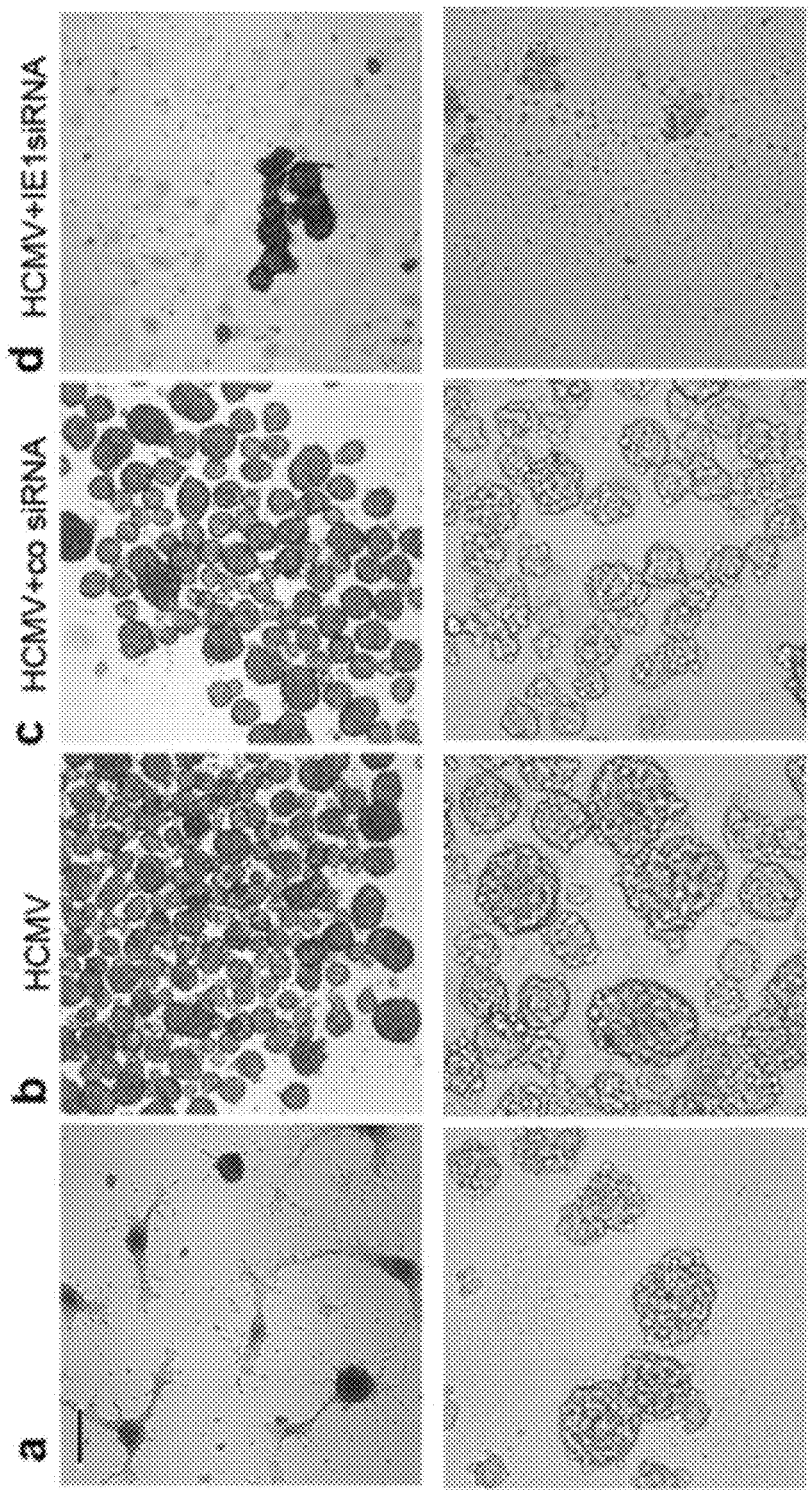
FIGURE 3A-D

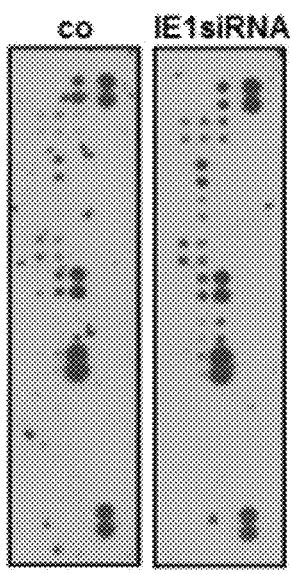
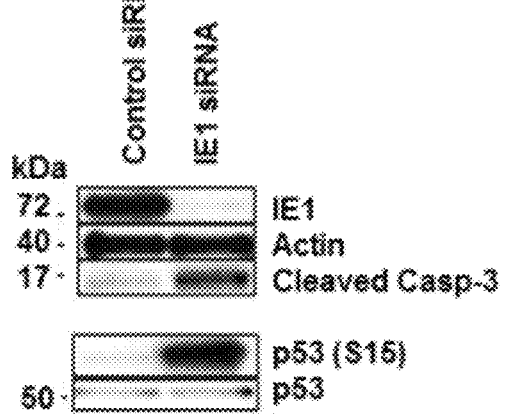
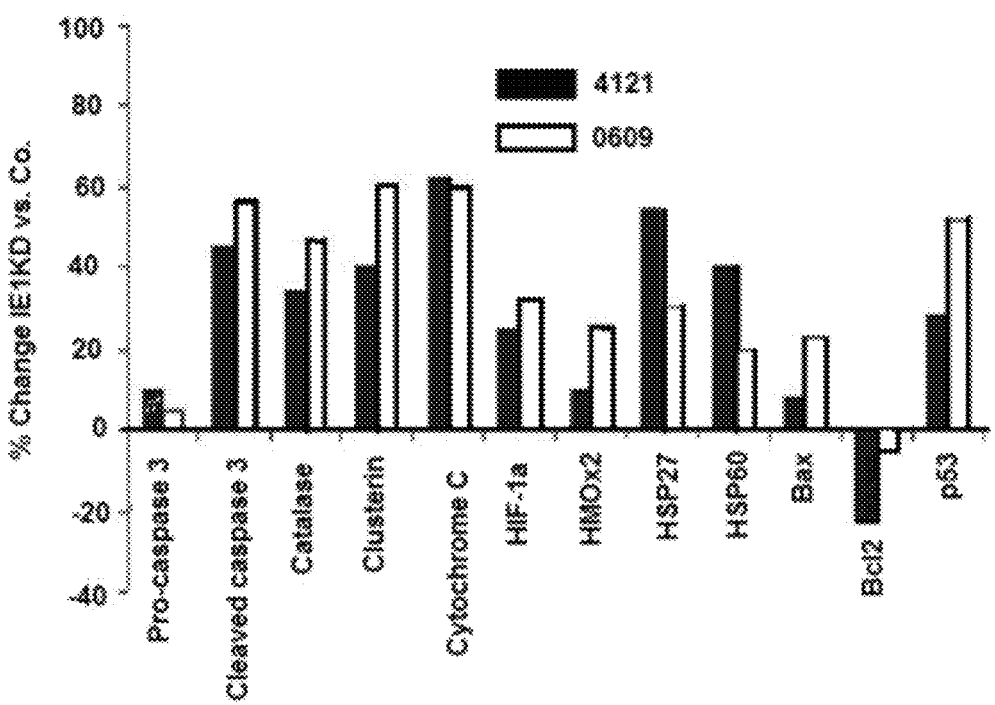
FIGURE 3E-G

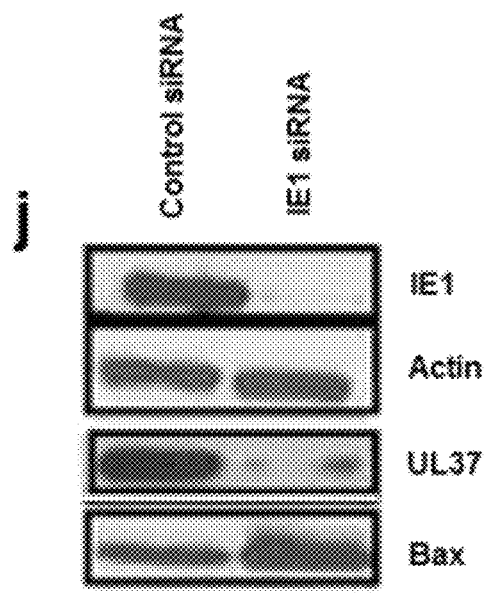
FIGURE 3J
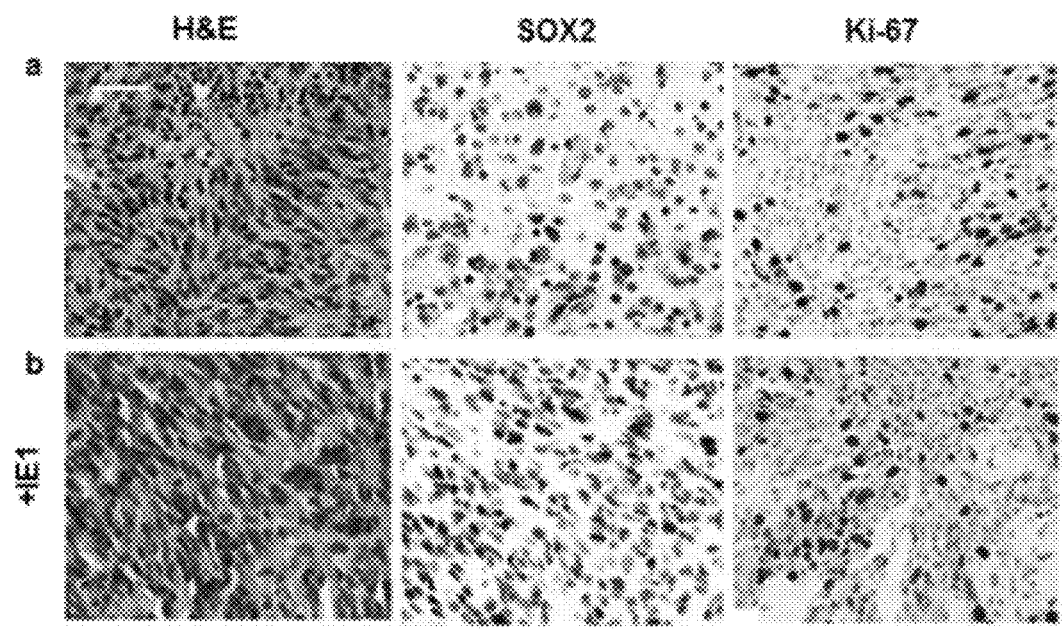
FIGURE 4A-B

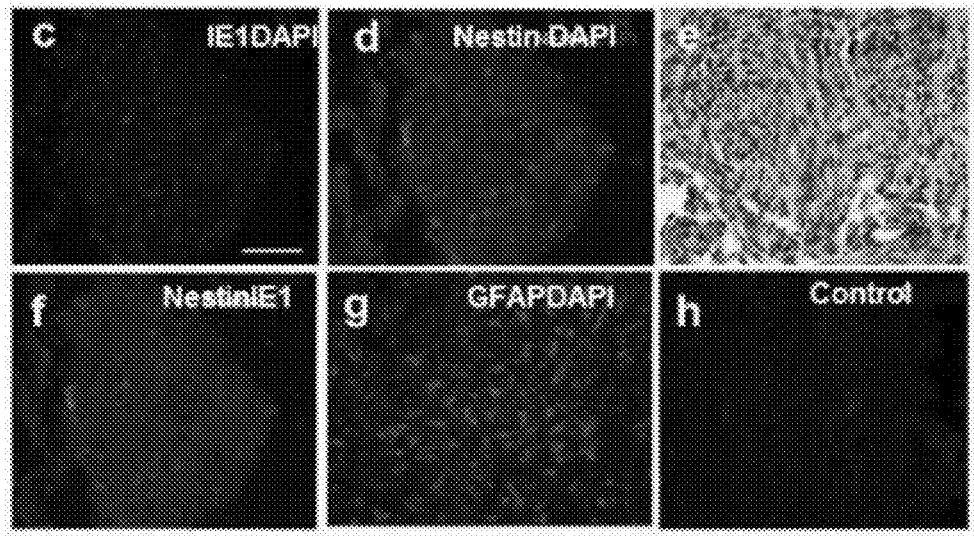
FIGURE 4C-H
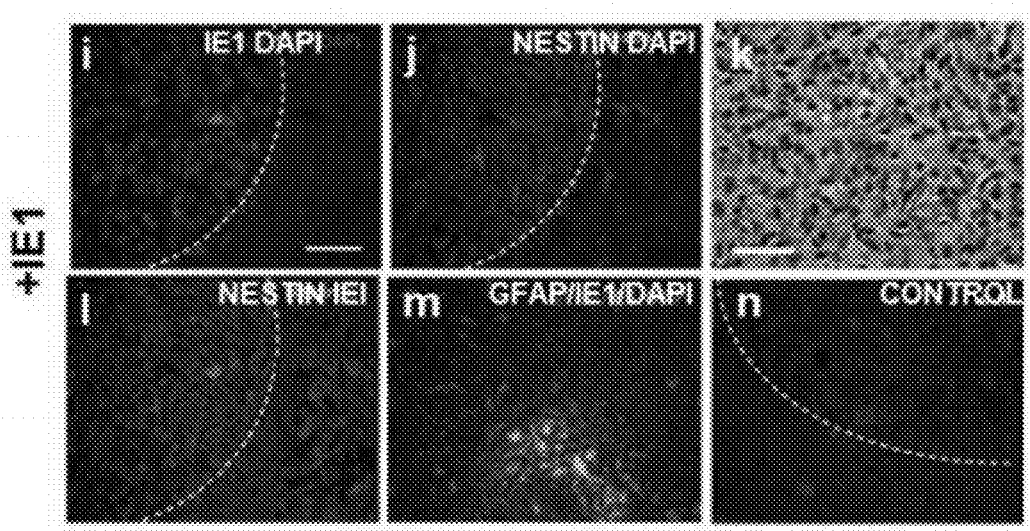
FIGURE 4I-N

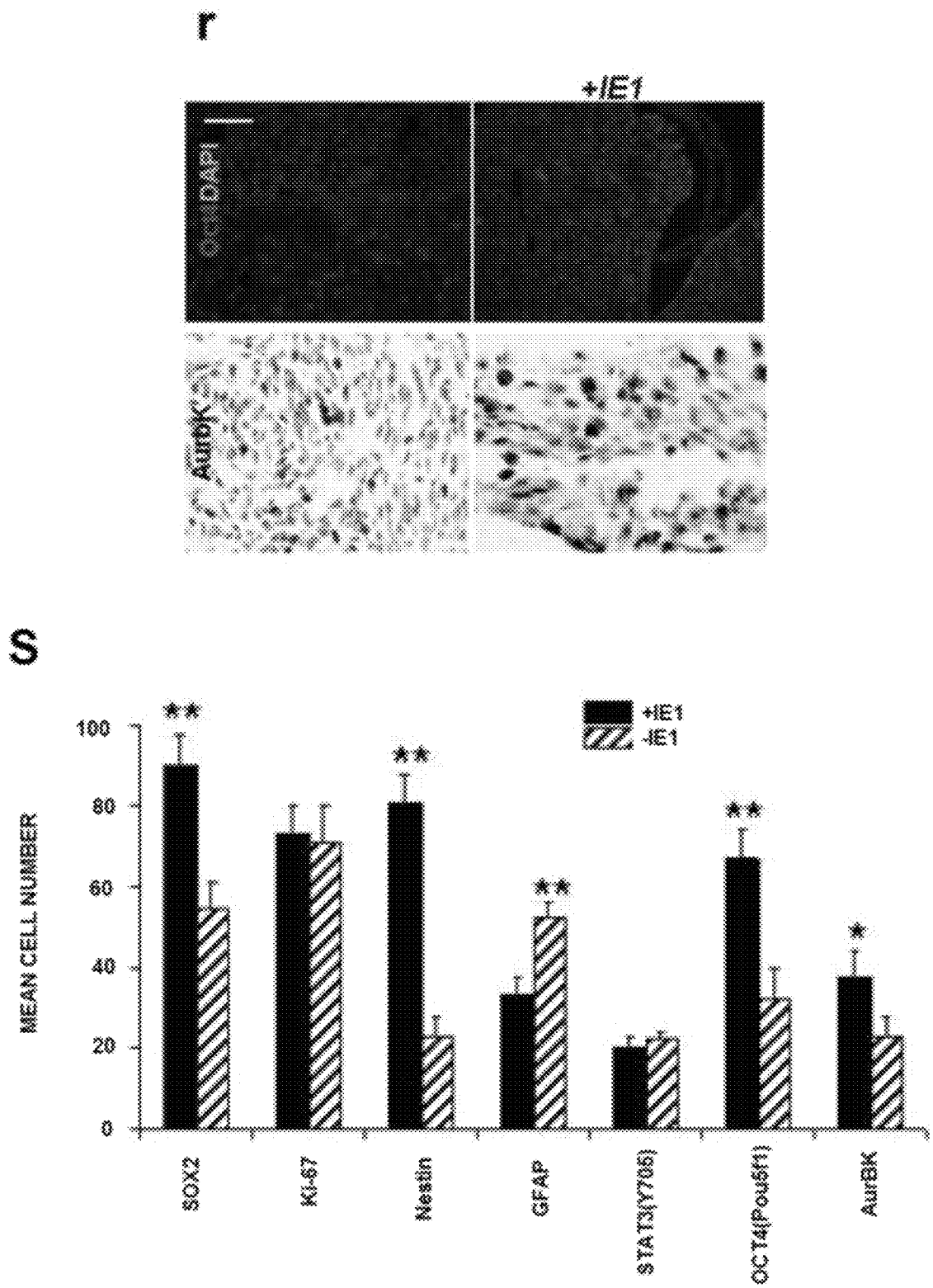
FIGURE 4R-S

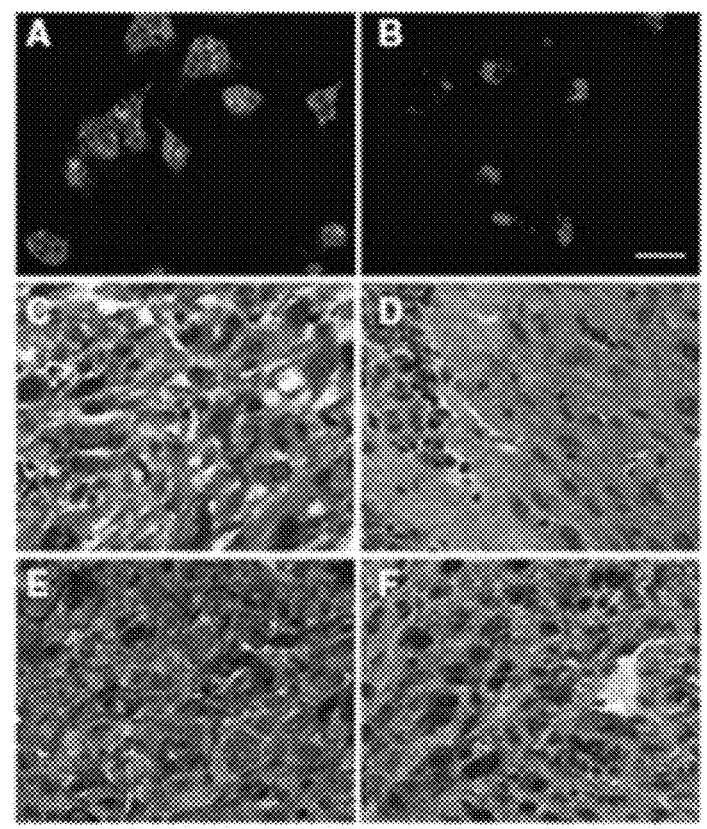
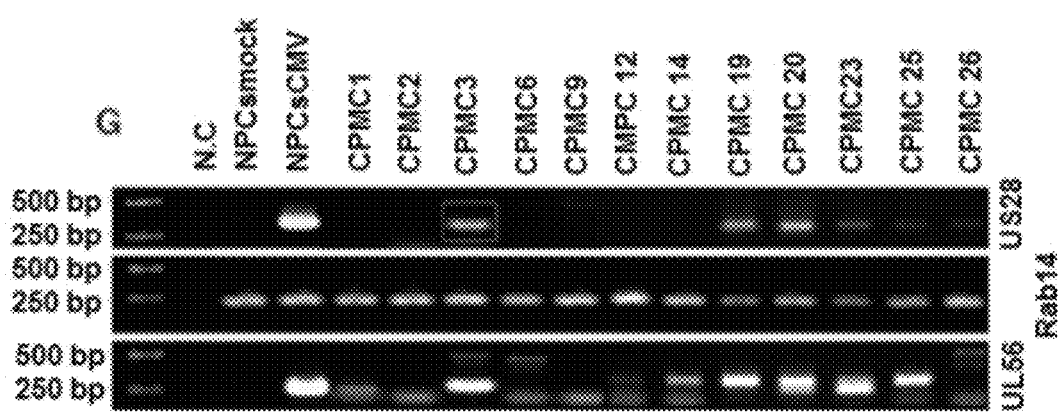
FIGURE 5A-G

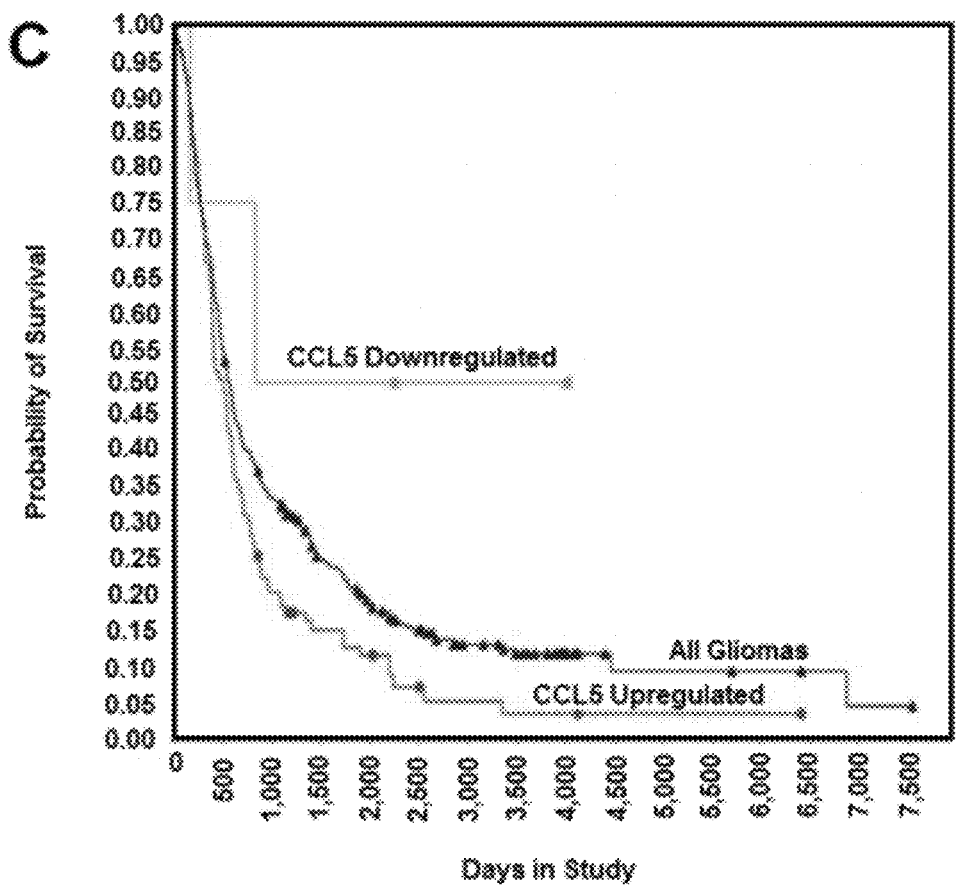
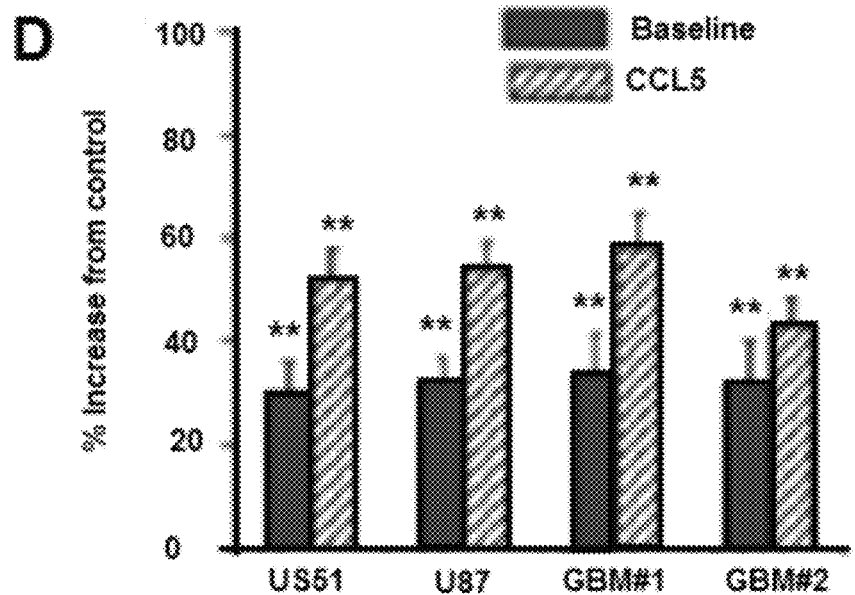
FIGURE 6C-D

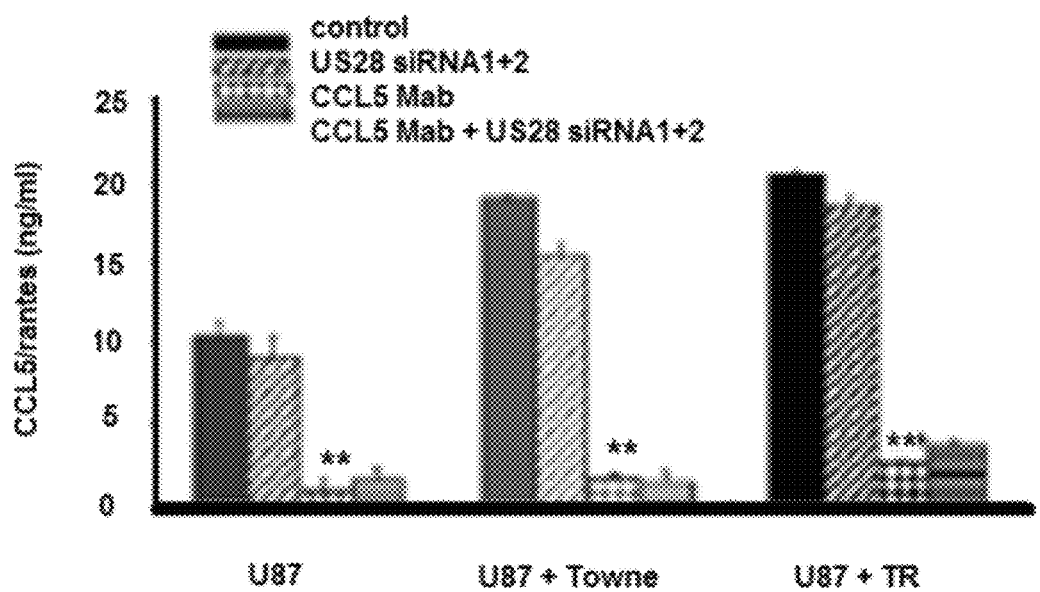
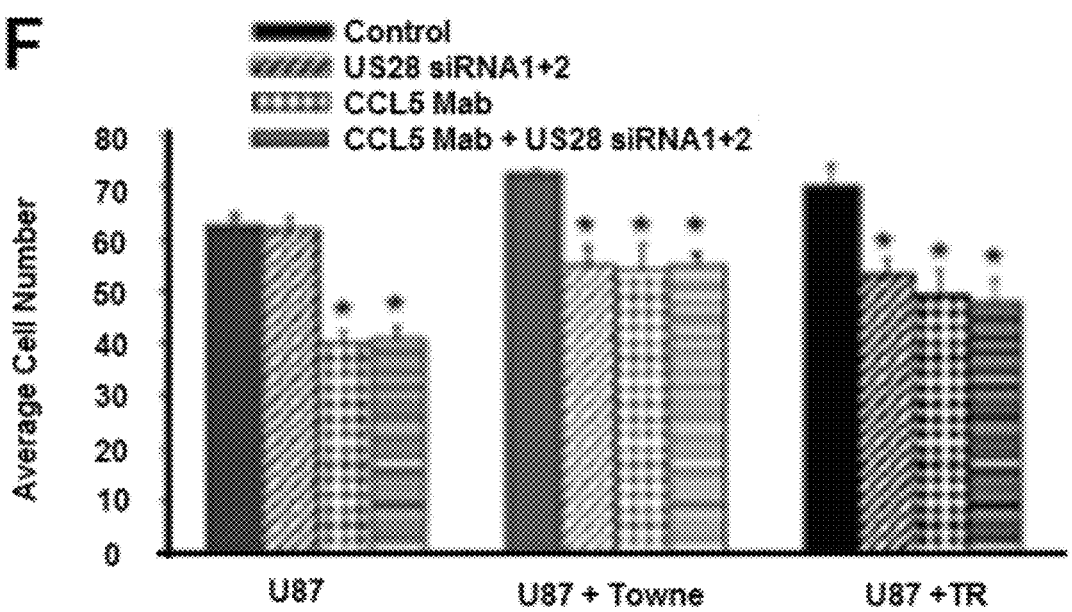
FIGURE 6E-F

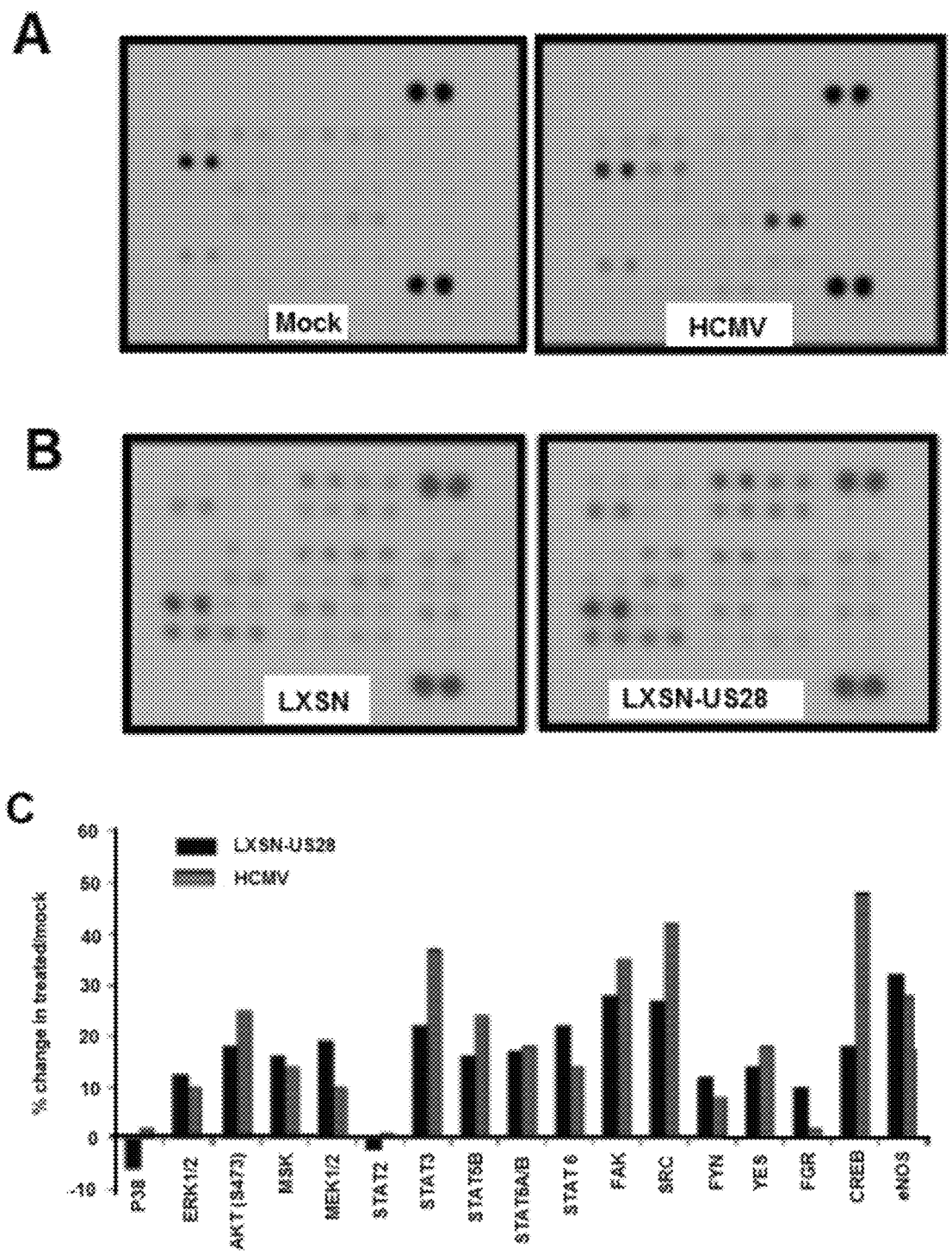
FIGURE 7A-C

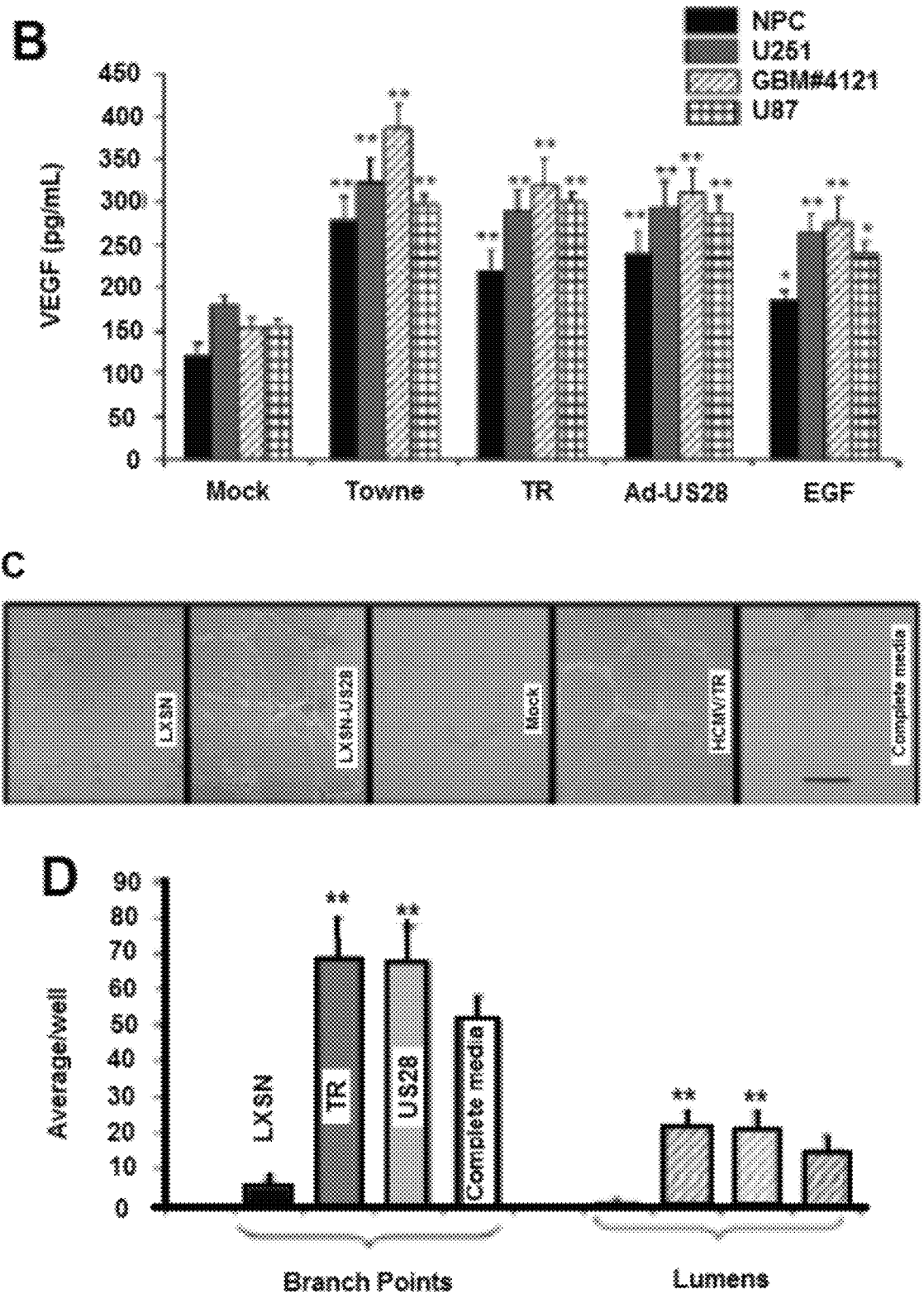
FIGURE 8B-D

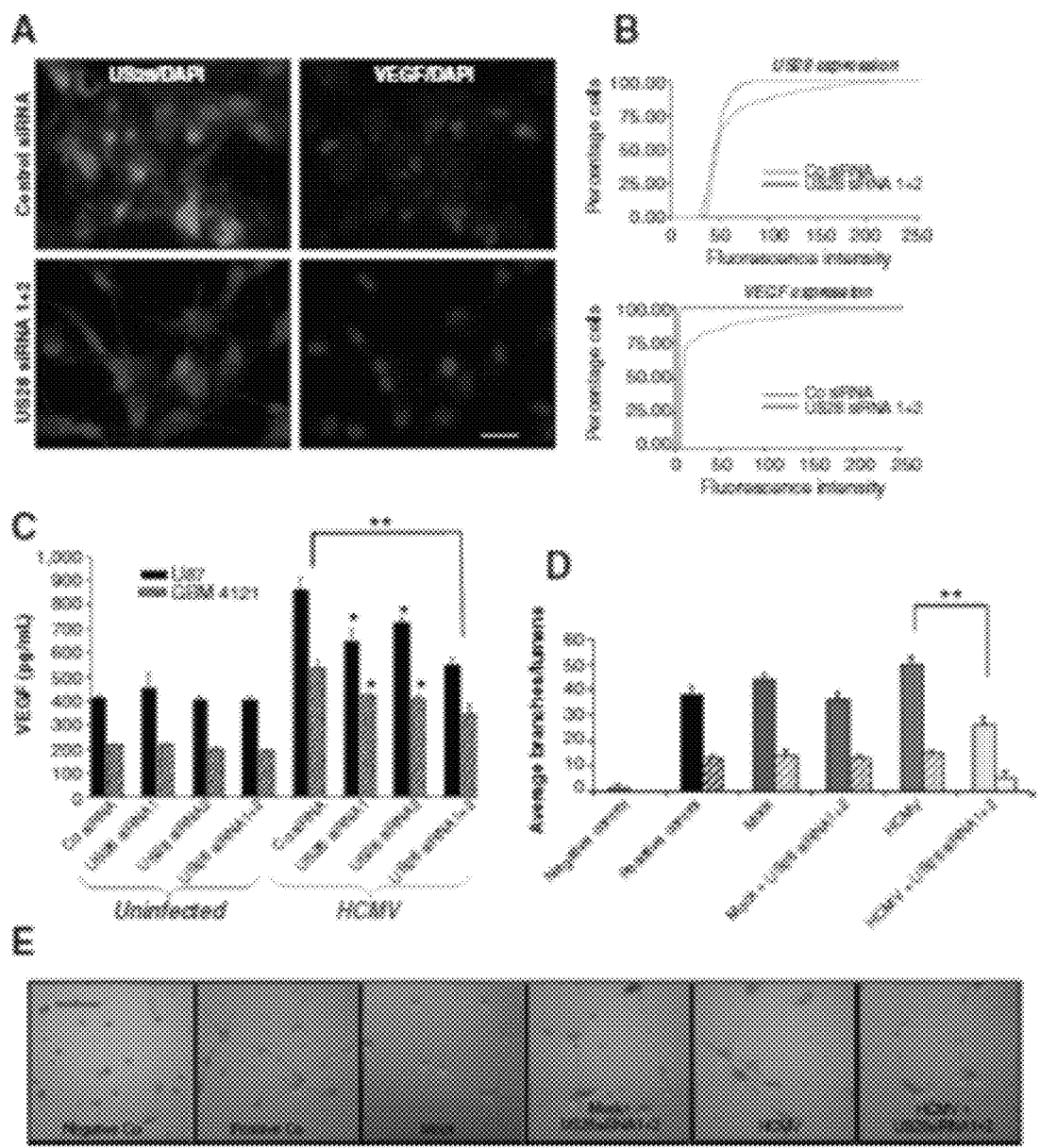
FIGURE 9A-E

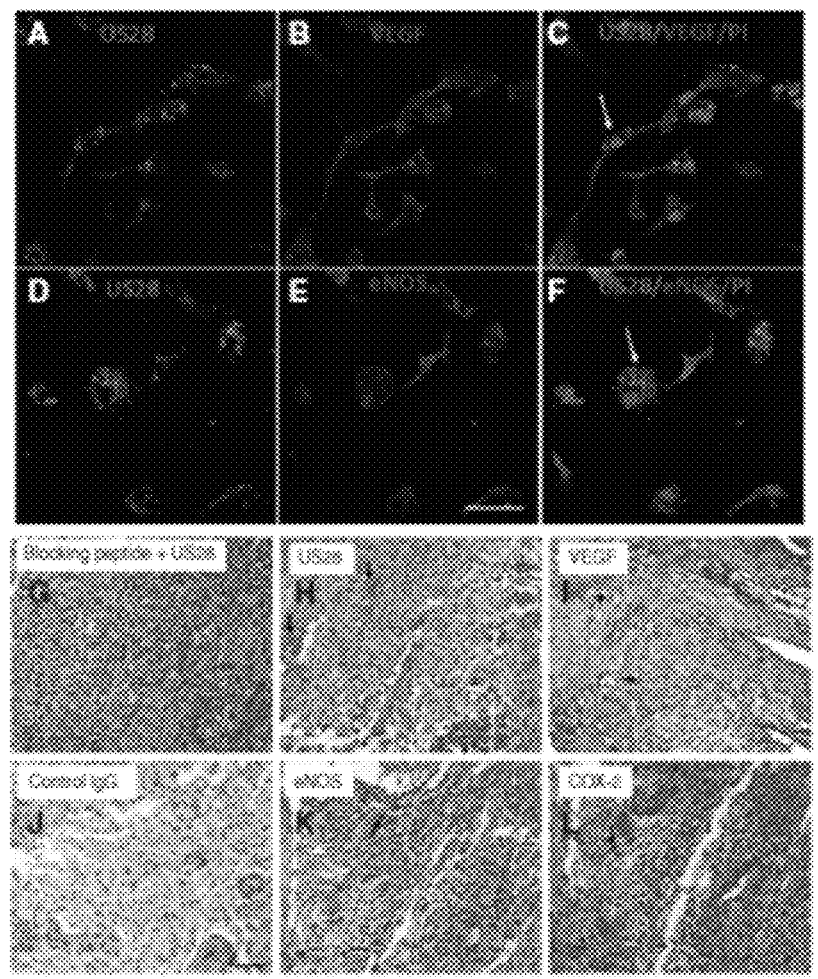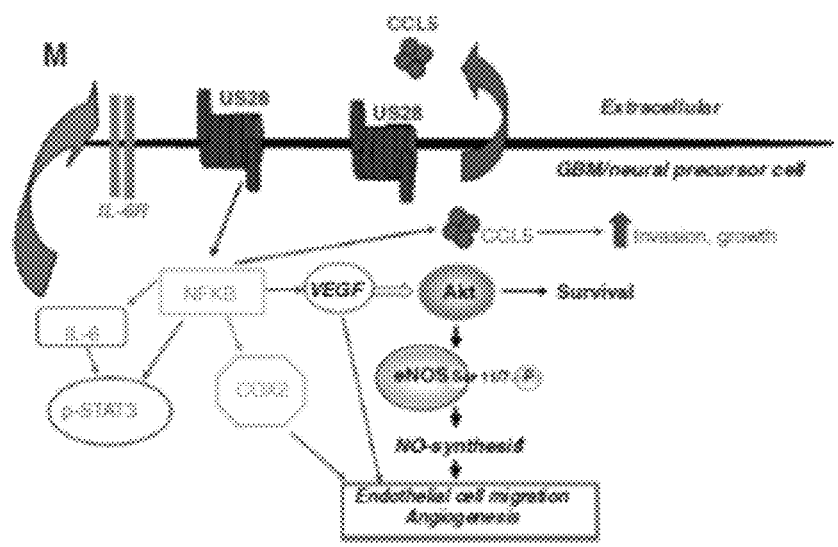
FIGURE 10A-M

```
                        SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide Primer/Probe

<400> SEQUENCE: 1
aagcggcctc tgataaccaa g                                              21

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide Primer/Probe

<400> SEQUENCE: 2
gagcagactc tcagaggatc g                                              21

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide Primer/Probe

<400> SEQUENCE: 3
catgcagatc tcctcaatgc ggcg                                           24

<210> SEQ ID NO 4
<211> LENGTH: 21
<212> TYPE: RNA
<213> ORGANISM: Artificial Sequence
<220> FEATURE:
```

<223> OTHER INFORMATION: Sense IE1KD siRNA

<400> SEQUENCE: 4
ggaaggaggu uaacagucau u                                         21

<210> SEQ ID NO 5
<211> LENGTH: 21
<212> TYPE: RNA
<213> ORGANISM: Artificial Sequence
<220> FEATURE:
<223> OTHER INFORMATION: Antisense IE1KD siRNA

<400> SEQUENCE: 5
ugacuguuaa ccuccuuccu u                                         21

<210> SEQ ID NO 6
<211> LENGTH: 21
<212> TYPE: RNA
<213> ORGANISM: Artificial Sequence
<220> FEATURE:
<223> OTHER INFORMATION: Sense IE1KD siRNA

<400> SEQUENCE: 6
ggaagaaagu gaacagaguu u                                         21

<210> SEQ ID NO 7
<211> LENGTH: 21
<212> TYPE: RNA
<213> ORGANISM: Artificial Sequence
<220> FEATURE:
<223> OTHER INFORMATION: Antisense IE1KD siRNA

<400> SEQUENCE: 7
acucuguuca cuuucuuccu u                                         21

<210> SEQ ID NO 8
<211> LENGTH: 23
<212> TYPE: RNA
<213> ORGANISM: Artificial Sequence
<220> FEATURE:
<223> OTHER INFORMATION: miR-145

<400> SEQUENCE: 8
guccaguuuu cccaggaauc ccu                                       23

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide Primer/Probe

<400> SEQUENCE: 9
agcaccatcc tcctcttcct ctg                                       23

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide Primer/Probe

<400> SEQUENCE: 10
aagcggcctc tgataaccaa gcc                                       23

<210> SEQ ID NO 11

```
<211> LENGTH: 23
<212> TYPE: DNA
<213> ORGANISM: Artificial Sequence
<220> FEATURE:
<223> OTHER INFORMATION: Oligonucleotide Primer/Probe

<400> SEQUENCE: 11
cagtgtttgg attggtgaga ttc                                              23

<210> SEQ ID NO 12
<211> LENGTH: 21
<212> TYPE: RNA
<213> ORGANISM: Artificial Sequence
<220> FEATURE:
<223> OTHER INFORMATION: US28 sense siRNA

<400> SEQUENCE: 12
cgacggaguu ugacuacgau u                                                21

<210> SEQ ID NO 13
<211> LENGTH: 18
<212> TYPE: RNA
<213> ORGANISM: Artificial Sequence
<220> FEATURE:
<223> OTHER INFORMATION: US28 sense siRNA

<400> SEQUENCE: 13
cucacaaauu accguauu                                                    18

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 14
gacgcgacac acctcgtcgg                                                  20

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide Primer/Probe

<400> SEQUENCE: 15
gcagatttgg gatacagcag g                                                21

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide Primer/Probe

<400> SEQUENCE: 16
cagtgtttgg attggtgaga ttc                                              23

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide Primer/Probe

<400> SEQUENCE: 17
```

```
gttgtttccc gaaagtttca ttat                                              24

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide Primer/Probe

<400> SEQUENCE: 18
cctctctcac aatgtggaca tg                                                22

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide Primer/Probe

<400> SEQUENCE: 19
gcagatttgg gatacagcag g                                                 21

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide Primer/Probe

<400> SEQUENCE: 20
tcgcgccaca aaggtcgcat                                                   20
```

CMV GENE PRODUCTS PROMOTE CANCER STEM CELL GROWTH

CROSS REFERENCE TO RELATED APPLICATIONS

This application claims priority from U.S. Provisional Application Ser. No. 61/476,234, filed Apr. 15, 2011, which is incorporated herein by reference.

TECHNICAL FIELD

The disclosure relates generally to compositions and methods useful for inhibiting the infection and propagation of viral particles, particularly members of the Herpesviridae family, and more particularly to Cytomegalovirus (CMV). The disclosure further relates to methods and related compositions for treating cancer. The methods and compositions comprise viral gene product inhibiting species.

BACKGROUND

Cytomegalovirus (CMV) is a member of Betaherpesvirinae in the subfamily Herpesviridae. CMV infects over 70% of the world's adult population and is the most common cause of congenital central nervous system (CNS) infection in humans. Clinically significant CMV disease frequently develops in patients immunocompromised by Human Immunodeficiency Virus (HIV), solid-organ transplantation, and bone-marrow transplantation. Additionally, congenital transmission from a mother with acute infection during pregnancy is a significant cause of neurological abnormalities and deafness in newborns.

Symptomatic disease in immunocompromised individuals can affect almost every organ of the body, resulting in fever of unknown origin, pneumonia, hepatitis, encephalitis, myelitis, colitis, uveitis, retinitis, and neuropathy. CMV establishes a latent infection in the host and may reactivate during a period of immunosuppression secondary to drugs or intercurrent infection.

In its latent state, the virus is known to reside in stem cells of the myeloid lineage and immune activation and differentiation of these cells can induce viral reactivation and replication. Stem cell populations in other organ systems are also likely to harbor persistent latent infection. Cellular differentiation state is tightly linked to viral expression patterns and this is thought to be due to differentiation-dependent chromatin remodeling of the viral major immediate-early (IE) promoter.

Additionally, association of CMV with several malignancies has been reported, including brain, breast, and colon cancers. A study has confirmed that CMV nucleic acids and proteins are detectable in over 90% of malignant gliomas. Furthermore, a significant proportion of these patients had detectable CMV in the peripheral blood, indicating the presence of an active viral infection.

Current treatment options for eradicating CMV infection includes antiviral agents such as Ganciclovir (a nucleoside analogue that inhibits DNA synthesis), Foscarnet (a DNA chain inhibitor of phosphorylation), Cidofovir (a nucleotide that inhibits DNA replication).

Glioblastoma multiforme (GBM) is a common, highly malignant primary central nervous neoplasm characterized by tumor cell invasion, robust angiogenesis and a mean survival of 15 months. hCMV infection is present in >90% of GBM in humans.

Current treatment options for cancer do not target implicated viruses. There exists a need for methods for such treatment and related compositions.

SUMMARY

The disclosure provides a method of treating or preventing a proliferative disease in a subject comprising administering an inhibitor of a IE1, US28 and/or pp71 or a homolog of any of the foregoing to the subject, wherein the inhibitor inhibits the expression or activity of the IE1, US28 and/or pp71 gene or polypeptide, respectively. In one embodiment, the proliferative disease is selected from the group consisting of heart disease, restenosis, lymphoproliferative disorders, multiple sclerosis, Kaposi's sarcoma, Stevens-Johnson syndrome, post-transplant lymphoproliferative disorder, chronic fatigue syndrome, Burkitt's lymphoma, nasopharyngeal carcinoma, inflammatory disease, organ rejection, transplant arteriosclerosis, myocarditis, retinitis, obliterative bronchiolitis and neoplastic disorders. In another embodiment, the proliferative disease is not graft versus host disease (GvHD). In yet another embodiment, the proliferative disease is associated with a herpes virus. In yet a further embodiment, the herpes virus is selected from the group consisting of CMV, EBV, HHV-6A, HHV-6B and HHV-7. In another embodiment, the proliferative disorder is glioblastoma multiforme. In one embodiment, the inhibitor of the IE1, US28 and/or pp71 or homolog is an inhibitory nucleic acid. In another embodiment, the inhibitory nucleic acid is an siRNA, ribozyme or triplex molecule. In an embodiment, the inhibitor of the IE1, US28 and/or pp71 or homolog is an inhibitory peptide. In one embodiment, the inhibitory peptide binds to IE1, US28 or pp71 polypeptide and inhibits activity of IE1, US28 or pp71. In another embodiment, the inhibitory nucleic acid has a sequence selected from the group consisting of SEQ ID NO:4, 5, 6, 7 and any combination thereof.

The disclosure also provides a method of treating a cell proliferative disease or disorder comprising exposing a cell infected with CMV to at least one small inhibitory RNA molecule (siRNA) that targets a CMV gene, under conditions that permit induction of ribonucleic acid interference (RNAi), such that cell proliferation, growth and/or migration of a cell infected with CMV is inhibited. In one embodiment, the siRNA targets a CMV immediate early gene. In another embodiment, the siRNA targets IE1. In yet another embodiment, the siRNA is a double stranded RNA (dsRNA) molecule, each strand of which is about 18-29 nucleotides long. In one embodiment, the dsRNA has a 3' dTdT sequence and a 5' phosphate group ($PO_4$). In another embodiment, each strand of the dsRNA is encoded by a sequence contained within an expression vector. In yet a further embodiment, the at least one siRNA comprises two different siRNA to two different target genes. In one embodiment, the at least one siRNA comprises three different siRNA to three different target genes. In another embodiment, the siRNA targets are selected from the group consisting of IE1, US28, pp71 and any combination thereof. In yet another embodiment, the siRNA is a double stranded RNA (dsRNA) molecule, each stand of which is about 18-29 nucleotides long. In yet a further embodiment, each strand of the dsRNA is encoded by a sequence contained within an expression vector.

The disclosure also provides an isolated nucleic acid for carrying out the methods described above comprising the sequence of SEQ ID NO: 4, 5, 6, 7, or a complement of any of the foregoing. In one embodiment, U is replaced by T. In yet another embodiment, the isolated nucleic acid is double-stranded. In yet a further embodiment, the isolated nucleic acid has 3' dTdT and 5'-PO₄. The disclosure also provides an RNAi agent which is targeted to a CMV nucleic acid encoding one or more CMV proteins selected from the group consisting of IE1, US28 or pp71. In one embodiment, the RNAi agent consists of dsRNA which is greater than about 18 nucleotides and less than about 29 nucleotides in length. The disclosure also provides a vector comprising the sequence of SEQ ID NO: 4, 5, 6, or 7 or a complement thereof. In one embodiment, U is replaced by T in the sequences set forth above. In another embodiment, the vector is a plasmid vector or a viral vector. In yet another embodiment, the vector expresses dsRNA greater than about 18 nucleotides and less than about 29 nucleotides in length.

The disclosure also provides a host cell comprising a vector as described above. In one embodiment, the host cell is infected with CMV.

The disclosure also provides a pharmaceutical composition comprising the isolated nucleic acid of the disclosure, the RNAi agent of the disclosure, or the vector of the disclosure, and a pharmaceutically acceptable carrier.

The disclosure also provides a method of treating a cell proliferative disease or disorder associated with CMV infection comprising administering the pharmaceutical composition above to a vertebrate mammal with the condition, such that the condition associated with CMV infection is treated. In one embodiment, the vertebrate mammal is a human patient. In another embodiment, the vertebrate animal is a non-human primate.

BRIEF DESCRIPTION OF DRAWINGS

FIG. 1A-O shows HCMV IE1 is preferentially expressed in human GSC. (A)-(B) RT-PCR and western blot analyses of human GBM and control samples for IE1 mRNA and protein. Rab 14 and Actin, loading controls. (C)-(E) Double immunofluorescence of GBM frozen section detecting CD133 (red) and IE1 (green); bar=100 µm. (F) CD133+ GSC neurospheres stained for IE1 (green) and Nestin (red), 48 h post-culturing; bar=200 µm. (G) GSC tumor sphere labeled for IE1 (green) and Sox2 (red); bar=50 µm. (H)-(K) Primary GSCs cultured on laminin labeled for IE1 (green) and PDGFRα (h), Sox2 (I), i-NOS (J), and integrin α6 (K), counterstained with DAPI (C)-(H) or propidium iodide (I)-(K) bar=100 µm. (L) RT-PCR analysis of primary GBM tissue and corresponding CD133+/− cell fractions. NB-normal brain; NC− no RT control. Rab14, loading control. (M) SSEA1+/− fractions analyzed by Taqman for IE1. Values normalized to GAPDH. (N)-(O) IE1 and actin western blots of GBM tissues (N) band corresponding CD133+/− cellular fractions (O). Negative and positive controls (HEL and U87+/−CMV) are shown.

FIG. 2A-J shows HCMV/IE1 promote self-renewal of GSCs by inducing Sox2 expression. (A) Photomicrographs of GSCs treated with control (left panels) or IE1 siRNA for 72 h. Bar=100 µm (B) 1° and 2° neurosphere assays+/− IE1siRNA. Average neurosphere numbers from four wells/condition are displayed. **$p<0.001$, *$p<0.01$, student t-Test. (C) GSC lysates from IE1 or control siRNA were hybridized to a stem cell antibody array (left panels); western blot analysis for the indicated proteins shown in right panels. (D) Relative abundance of miR-145, normalized to RNU48 levels, measured by Taqman. (E) Western blot analysis of HCMV and mock-infected GSCs for indicated proteins. (F) miR-145 levels measured by Taqman in GSCs pre-treated with anti-miR-145, 48 h prior to HCMV infection. **$p<0.0001$, *$p<0.02$, student T-test. Samples were run in quadruplicate and the experiment was repeated twice. (G) Western blot detection of IE1, Sox2, Oct4 in GSC treated as indicated.

Figure 3H:
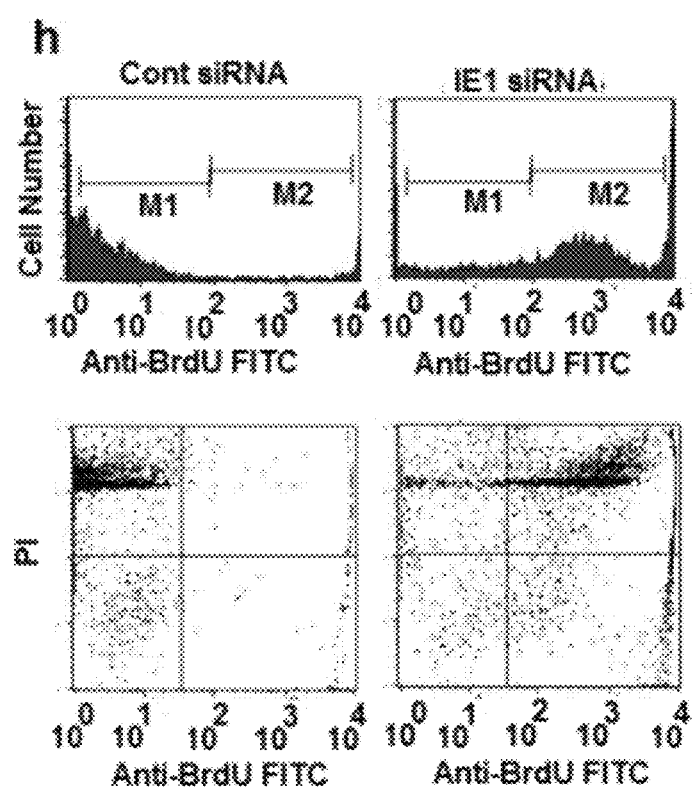

(H)-(I). Representative photomicrographs of GSC neurospheres (bar=100 µm) quantified at 72 h (4 wells/condition, repeated twice). *$p<0.01$, student T-test. (J) Proposed mechanism for HCMV/IE1 regulation of miR-145-Sox2-Oct4 network.

FIG. 3A-J shows IE1KD Induces apoptosis in HCMV-positive GSC. (A)-(B) Photomicrographs of HCMV negative 4121 and 0609 GSCs 72 h after mock (A) or HCMV (B) infection; bar=50 µm. Cells photographed 48 h after treatment with control or (C) IE1 siRNA (D). Each condition was run in triplicate and repeated twice. (E) Lysates of HCMV-infected 4121 GSC, treated with indicated siRNAs and hybridized to an apoptosis antibody array. (F) Western blots of the same samples as in e for indicated proteins. (G) Quantification of relative changes in apoptotic proteins shown in (E). (H) Representative example of FACS analysis, showing a ~70% right shift of the M2 (apoptotic) cell peak induced by IE1KD. (I) Heatmap displays significantly down-regulated CMV transcripts following IE1KD in 4121 and 0609 GSCs. Arrows, UL123 (IE1) and UL37. (J) Western blot detection of indicated proteins in HCMV-infected 0609 GSC treated with siRNA, as shown.

FIG. 4A-S shows IE1 expression augments glioma stem cell phenotype in vivo. (A)-(B) H&E, Sox2, and Ki-67 immunohistochemical analysis of representative mouse gliomas induced by p53 KD/PDGF/NRasV12 in the absence (A) or presence (B) of IE1. Bar=50 µm. (C)-(N) Immunofluorescence analysis of control (C-H) and IE1 (I-N) expressing mouse gliomas. 5 µm sequential sections were stained for IE1 (c, i), Nestin (D, J), GFAP (G, M) and doubly labeled (F, L, M). Control IgG (H, N) and H&E staining (E, K). Bar=50 µm. (O). Hierarchical clustering (by genes and samples) of 27,368 autosomal gene transcripts in 6 mouse gliomas+/−IE1. Log 2 ratios range −0.5 (blue) to +0.5 (red). (P) IPA analysis of transcripts significantly up-(+2×, red) and down-regulated (−2×, green) in IE1+ tumors. (R) Representative photomicrographs of Oct 4 (upper panels) and Aurora B kinase (lower panels) immunohistochemical detection in IE1+/− mouse gliomas, bar=150 µm. (S) Four 10× fields from 6 tumors/group were counted for each marker. Mean counts/100 nuclei are shown. **$p<0.003$, *$p<0.01$, student t-Test.

FIG. 5A-G shows HCMV US28 transcript and protein are expressed in human GBMs. A and B, primary GBM-derived cultures were processed for US28 immunofluorescence in the absence (A) or presence (B) of a blocking peptide. Nuclei are counterstained with propidium iodide. Bar, 100 µm. C-F, consecutive (5 µm) paraffin sections obtained from a different GBM patient sample were processed for US28 (C and D), VEGF (E), and COX2 (F) immunohistochemistry. Counterstaining, hematoxylin. Bar, 100 µm. G, reverse transcriptase PCR for US28 was done using cDNA from several GBM cases. HCMV-infected neural precursor cells (NPC+CMV) served as positive controls. Several cases show a US28 band of the correct size. HCMV UL56 detection is also shown. Rab14 was used to verify equal loading. NC, negative control.

FIG. 6A-F shows US28-CCL5 signaling promotes glioblastoma invasiveness. A, NPCs infected with Towne and TR HCMV strains (MOI=1, 72 hours) were profiled with an HCMV DNA microarray containing all predicted ORFs for Ad169/Toledo strains. Expression levels of HCMV transcripts are displayed as fold increase over uninfected control. B, RNA from HCMV-treated and control NPCs were profiled with Affymetrix Gene 1.0 ST DNA arrays. The heatmap shows the 30 most upregulated and 30 most downregulated human transcripts in HCMV-infected NPCs versus mock. CCL5 was induced more than 40-fold by HCMV treatment (arrow). C, Kaplan-Meier curves showing the relationship between levels of CCL5 transcript and survival probability in patients with glioblastoma (log-rank P value upregulated vs. all other samples, P=0.001523, REMBRANDT database, National Cancer Institute). D, human glioma cells (U251 and U87) and 2 primary glioblastoma-derived cultures (designated GBM#1 and GBM#2) transfected with US28 or control vector were subjected to Matrigel invasion assays in the absence or presence of CCL5 (50 ng/mL). , P<0.005, ANOVA. E, CCL5 levels measured by ELISA in mock-treated U87 cells or HCMV-infected with or without CCL5-neutralizing antibody. , P<0.005, ANOVA. F, mock-treated and HCMV-infected U87 cells were subjected to Matrigel invasion assays. Mean number of cells per filter is shown for each condition. **, P<0.005, ANOVA. US28 knockdown was achieved with 2 siRNA duplexes in combination (siRNA1+2). Data from 1 representative experiment are shown. Each experiment was carried out in triplicate, and experiments were repeated 3 times.

FIG. 7A-D shows US28 induces activation of cellular kinases involved in glioma pathogenesis. A and B, HCMV (Towne; MOI=1) and mock-treated NPCs (A) and glioma cells (B) were profiled with a phosphor-kinase human antibody array. C, densitometry measurements were done per the manufacturer's instructions. Percentage of change in phosphorylation levels between HCMV/US28-treated and control cells is shown. One (of 2) representative experiment is shown. D, double immunofluorescence for US28 and the indicated proteins in NPCs transduced with LXSN-US28 for 48 hours. Right, IgG staining controls. Nuclei were counterstained with propidium iodide. Bar, 50 μm.

FIG. 8A-D shows US28 promotes glioma angiogenesis. NPCs transduced with either LXSN-HA-US28 or Ad-US28 and control LXSN/mock-treated cells were processed for immunofluorescence. Right, NPCs that express US28 secrete VEGF, as shown by colocalization of the 2 markers. Nuclei are stained with propidium iodide. Bar, 100 μm. B, NPC, U251, U87, and a primary GBM line (4121) were treated with HCMV (Towne and TR; MOI=1), transduced with Ad-US28, or treated with EGF (50 ng/mL) in serum-free media. Supernatants were used in an ELISA for VEGF. Samples were assayed in quadruplicate, and the experiment was repeated twice. Comparisons between treated and mock within the same cell line were analyzed by ANOVA. *, P=0.02; , P<0.002. C, NPC-derived supernatants were tested in HUVEC tube formation assays. Complete endothelial cell growth media was used as a positive control. Representative photomicrographs are shown. Each condition was assayed in 6 wells of a 24-well plate, and the experiment was repeated twice. Bar, 100 μm. D, average numbers of branch points and endothelial cell lumens are shown from 1 representative experiment. Comparisons were analyzed by ANOVA. , P<0.02 in all cases.

FIG. 9A-E shows US28 knockdown in HCMV-infected glioma cells inhibits VEGF secretion and subsequent angiogenesis. A, immunofluorescence was used for detection of US28 (green) and VEGF (red) in U87 cells persistently infected with HCMV treated either with control siRNA (top) or siRNA1+2 targeting US28. Nuclei were counterstained with DAPI. Bar, 50 μm. B, cumulative distribution of mean pixel intensity per cell obtained from immunofluorescence detection of US28 and VEGF in U87 cells treated with either targeting (siRNA1+2) or control siRNAs. The Kolmogorov-Smirnov test was used to determine significance of differences in the fluorescence intensity measured in more than 100 cells per condition, P=0.0001. C, VEGF levels were measured by ELISA in U87 glioma cells and primary 4121 GBM cells uninfected or HCMV-infected in the presence of either control or US28 targeting siRNA1, siRNA2, or siRNA1+2. Differences were significant. *, P=0.05; , P=0.002, the Student t test. D, quantification of HUVEC branches and lumens formed in each of the indicated conditions. , P<0.02, ANOVA. E, representative photomicrographs of HUVEC tube formation assay in the presence of various types of conditioned media, as indicated. Bar, 100 μm. HUVEC tube formation assays were repeated 3 times, each condition was run in quadruplicate.

FIG. 10A-G shows HCMV US28 colocalizes with markers of invasiveness and angiogenesis in situ. A-F, primary glioblastoma-derived cells were processed for immunofluorescence with antibodies against US28 (A and D), VEGF (B), and e-NOS (E). C and F, merged photomicrographs of colocalization of US28 and the 2 markers of angiogenesis. Nuclei are counterstained with propidium iodide. Bar, 100 μm. G-L, consecutive paraffin sections (5 μm apart) from a glioblastoma specimen were stained for US28, VEGF, e-NOS, and COX2 and developed with horseradish peroxidase-3,3'-diaminobenzidine. Arrows indicate cells positive for several markers in the same area. Counterstaining, hematoxylin. Bar, 50 μm. M, summary of the autocrine and paracrine signaling pathways through which US28 promotes GBM growth, invasion, and angiogenesis.

DETAILED DESCRIPTION

As used herein and in the appended claims, the singular forms "a," "and," and "the" include plural referents unless the context clearly dictates otherwise. Thus, for example, reference to "a cell" includes a plurality of such cells and reference to "the viral particle" includes reference to one or more viral particles known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications herein are provided solely for their disclosure prior to the filing date of the present application. Nothing herein is to be construed as an admission that the inventors are not entitled to antedate such disclosure by virtue of prior disclosure.

Human herpesvirus 5 (human cytomegalovirus; HCMV) is a ubiquitous human herpesvirus that can cause life threatening disease in the fetus and the immunocompromised host. Upon attachment to the cell, the virus induces robust inflammatory, interferon- and growth factor-like signaling. HCMV causes a persistent infection that occurs in over 70% of adults. Association of HCMV infection with several human malignancies, including brain, prostate, and colon cancer have been reported (Harkins et al., 2002), suggesting a potential role for HCMV in oncogenesis.

HCMV is present in over 90% of human malignant gliomas, while no viral gene products were detectable in the non-malignant brain tissue. These findings have important implications for glioma biology, since accumulating evidence indicates that HCMV viral gene products can alter signaling pathways underlying cellular apoptosis, proliferation, migration, and transformation. For example, transcriptional activation of cellular oncogenes, including c-FOS, c-MYC and c-JUN are induced by HCMV exposure, reminiscent of growth factor-mediated signaling events. This activation does not require viral infectivity or de novo viral protein synthesis.

In addition, HCMV infections are routinely encountered and increase morbidity and mortality in transplant patients and are associated with congenital CMV infection, perinatal CMV infection, immunocompetent patient, CMV mononucleosis, post-transfusion CMV—similar to CMV mononucleosis, immunocompromised patient (such as HIV patients), CMV pneumonitis, CMV GI disease, and CMV retinitis.

In efforts to exert cell cycle control and inhibit apoptosis, DNA viruses have acquired the capacity to subvert cellular signaling pathways, most notably by activation of the PI3-K/AKT axis, or interference with p53 and Rb cell cycle control functions (Cooray, 2004, O'Shea, 2005). For example, activation of the PI-3K/AKT pathway is central to the ability of human herpesvirus 4 (Epstein-Barr virus; EBV) to establish viral latency and to induce transformation of B cells and of the oropharyngeal epithelium, leading to nasopharyngeal carcinoma (Cooray, 2004, Dawson et al., 2003).

The disclosure provides methods to treat CMV related disease and disorders by inhibiting the action of viral genes that subvert cellular pathways to promote cell migration, proliferation and growth.

The data provided herein demonstrate that certain HCMV genes promote cell proliferation and induce oncogene expression thereby promoting cells to take on a cancerous phenotype. The methods and compositions of the disclosure can be used to treat cell proliferative disorders associated with HCMV gene expression.

For example, HCMV proteins are expressed in various cell types within the glioma PVN and regulate autocrine and paracrine signaling. The disclosure demonstrates in one embodiment, that IE1 is preferentially expressed in the glioma stem cell compartment, wherein it modulated glioma stem cell growth and expression levels of stem cell markers.

As used herein, the term "IE-1" or "HCMV IE-1" or "IE-1 antigen" or similar term shall be taken to mean a polypeptide of HCMV having the publicly available amino acid sequence deposited under NCBI Accession No. P13202 (Chee et al., Curr. Top. Microbiol. Immunol 154, 125-169, 1990), and preferably having the expression profile of an immediate-early HCMV protein, or a related polypeptide of HCMV or other β-herpesvirus of humans having at least about 80% amino acid sequence identity to said sequence. Those skilled in the art will be aware that the IE-1 polypeptide of HCMV is also termed "UL123".

Similarly, the term "IE1 gene" or "IE1 polynucleotide" refers to a nucleic acid sequence that encodes the IE1 polypeptide or IE1 antigen as identified above. The IE1 polynucleotide has the sequence as set forth in NCBI Accession No. M21295 (the disclosure of which is incorporated herein by reference).

As described herein, expression of IE1 causes induction of pathways that cause cell migration, proliferation and growth of cells. Thus, inhibiting IE1 activity can inhibit cell migration, proliferation and growth, such as that associated with cancer cells associated with an hCMV infection. Accordingly, in one embodiment an IE1 antagonist is used to treat a cell proliferative disorder associated with CMV infection. An IE1 antagonist includes an agent that inhibits the activity or expression of IE1 gene product or gene, respectively. Such IE1 antagonists include antibodies that specifically interact with an IE1 gene product and inhibit IE1 function or an inhibitory nucleic acid that inhibits the expression (e.g., transcription or translation) of the IE1 gene or polynucleotide. Useful IE1 inhibitory nucleic acids include siRNA, RNAi, ribozymes, antisense molecules and the like.

As will be apparent from the sequences set forth in the accession numbers above, one of skill in the art can readily design and produce antigens for producing antibodies against and IE1 polypeptide. Similarly using the polynucleotide sequence of IE1, one of skill in the art can design and produce siRNA and other inhibitory nucleic acid sequences the inhibit expression of an IE1 polypeptide.

Additional data described below demonstrate intercellular signaling between tumor and endothelial cells regulated by HCMV proteins such as the US28 (a CXCR1 viral homologue)-p-STAT3-VEGF axis.

The disclosure demonstrates that HCMV-US28 is associated with cancer cells. US28 is an HCMV-encoded G-protein-coupled receptor that is a homologue of the human CCR1 chemokine receptor. US28 is constitutively active and may be further activated by binding of several ligands: SDF-1, CCL2/MCP-1, CCL5/RANTES, and CX3CL1/Fraktalkine. US28 has properties of a viral oncogene, because ectopic expression of US28 can induce a proangiogenic and transformed phenotype in vivo via activation of the NF-κB and COX2 signaling pathways. A recent report showed that US28 induces interleukin-6 (IL-6) and VEGF through NF-κB activation, resulting in potent activation of the STAT-3 transcriptional activator in NIH 3T3 mouse fibroblasts.

"US28" refers to open reading frame 28 in the unique short region of the genome of human strains of CMV and the protein encoded by this reading frame; while US28 can refer to either the coding region or the corresponding protein, is some instances the term US28 protein or US28 nucleic acid is used for the sake of increased clarity. US28 can be identified from GenBank accession no. L20501 and GenBank accession no. AF073831 (the disclosure of which are incorporated herein by reference). The term US28 includes other US28 molecules, e.g., derived from other clinical strains of human CMV, that differ slightly in sequence (see, e.g., GenBank accession nos. AF 073832-35; see also M. S. Chee, et al. (1990) Curr. Top. Microbiol. Immunol. 154:125-69).

As described herein, expression of US28 causes induction of angiogenic stimuli that promote proliferation and growth of cells. Thus, inhibiting US28 activity can inhibit cell migration, proliferation and growth, such as that associated with cancer cells having an hCMV infection. Accordingly, in one embodiment a US28 antagonist is used to treat a cell proliferative disorder associated with CMV infection. A US28 antagonist includes an agent that inhibits the activity or expression of a US28 gene product or gene, respectively. Such US28 antagonists include antibodies that specifically interact with a US28 gene product and inhibit US28 function or an inhibitory nucleic acid that inhibits the expression (e.g., transcription or translation) of the US28 gene or polynucleotide. Useful US28 inhibitory nucleic acids include siRNA, RNAi, ribozymes, antisense molecules and the like.

Furthermore, the disclosure also demonstrates that pp71 induces stem cell factor (SCF), an angiogenic molecule that binds its endothelial cell receptor (c-Kit) to promote capillary tube formation. The disclosure demonstrates that the HCMV tegument protein, pp71, performs many functions to enhance the efficiency of viral gene expression and replication. At the start of infection, pp71 stimulates viral immediate early gene expression by degrading the cellular repressor protein Daxx.

Daxx localizes to the nuclear promyelocytic leukaemia (PML) bodies which act as a reservoir for transcriptional regulators, antiviral response mediators, and tumor suppressors. Degradation of Daxx in conjunction with sumoylation of PML by the viral protein IE1 results in the dispersal and dysregulation of associated cellular regulatory proteins during infection. pp71 has also been demonstrated to degrade the hypophosphorylated form of the reinoblastoma (Rb) tumor suppressor protein in fibroblasts, thus promoting cell cycle progressions into S-phase and downregulate MHC class I cell surface expression in glioblastoma cells to facilitate immune evasion.

The disclosure used expression profiling to identify the presence of pp71 in glioblastoma multiforme (GBM). pp71 expression was identified in several primary GBM tissue samples. In addition, the disclosure demonstrates that pp71 expression in normal neural precursor cells stimulates the expression and secretion of the pro-angiogenic cytokine, stem cell factor (SCF). The disclosure demonstrates that pp71 promotes oncomodulatory effects of HCMV in primary gliomas.

As used herein, the term "pp71" or "HCMV pp71" or "pp71 antigen" or similar term shall be taken to mean a polypeptide of HCMV having the publicly available amino acid sequence deposited under NCBI Accession Nos. NP 040017, CAA35356 or P06726 (Chee et al., Curr. Top. Microbiol. Immunol 154, 125-169, 1990; Ruger et al., J Virol., 61, 446-453, 1987; and Bankier et al., DNA Seq 2, 1-12, 1991), and preferably having the function of an upper matrix phosphoprotein as described by Ruger et al., J. Virol., 61, 446-453, 1987, or a related polypeptide of HCMV or other β-herpesvirus of humans having at least about 80% amino acid sequence identity to said sequence. Those skilled in the art will be aware that the pp71 polypeptide of HCMV is also termed "UL82".

Stem cell factor (also known as SCF, kit-ligand or steel factor) is a cytokine that binds to the c-kit receptor tyrosine kinase (CD117) and is involved in hematopoesis, spermatogenesis, and melanogenesis. The c-kit receptor is expressed on hematopoetic stem cells, germ cells and progenitor cells derived from the neural crest. This receptor is a proto-oncogene and is activated in several types of human tumors, such as gastrointestinal stromal tumors (GIST), small-cell lung carcinoma, leukemias, melanoma, and germ cell tumors. SCF, which exists in both a membrane-bound and a secreted form, is produced by fibroblasts and endothelial cells and promotes cell survival, proliferation, and differentiation by activating multiple signaling cascades downstream of c-kit, including the RAS/ERK, PI3-kinase, Src kinase and Jak/STAT pathways. Importantly, SCF/c-kit activation has been shown to promote recruitment of endothelial progenitor cells to stimulate angiogenesis in ischemic environments, a process which is essential to the growth and maintenance of tumors.

As described herein, expression of pp71 causes induction of stimuli that promote dysregulation of the cell cycle, proliferation and growth of cells. Thus, inhibiting pp71 activity can inhibit proliferation and growth, such as that associated with cancer cells having an hCMV infection. Accordingly, in one embodiment a pp71 antagonist is used to treat a cell proliferative disorder associated with CMV infection. A pp71 antagonist includes an agent that inhibits the activity or expression of a pp71 gene product or gene, respectively. Such pp71 antagonists include antibodies that specifically interact with a pp71 gene product and inhibit pp71 function or an inhibitory nucleic acid that inhibits the expression (e.g., transcription or translation) of the pp71 gene or polynucleotide. Useful pp71 inhibitory nucleic acids include siRNA, RNAi, ribozymes, antisense molecules and the like.

Taken together the data provide support that several HCMV regulatory signaling mechanisms are active in cancer cells. That these HCMV regulatory signaling pathways induce a cancerous phenotype and promote proliferation, migration and growth of cells.

As will be apparent from the sequences set forth in the accession numbers above, one of skill in the art can readily design and produce antigens for producing antibodies against and US28, IE1, and pp71 polypeptides. Similarly, using the polynucleotide sequence of US28, IE1 and pp71, one of skill in the art can design and produce siRNA and other inhibitory nucleic acid sequences the inhibit expression of a US28, IE1 or pp71 polypeptide.

For example, a pharmaceutical composition comprising a US28, IE1 and/or pp71 antagonist can be administered to a patient either by itself (complex or combination) or in pharmaceutical compositions where it is mixed with suitable carriers and excipients. A US28, IE1 and/or pp71 antagonist can be administered parenterally, such as by intravenous injection or infusion, intraperitoneal injection, subcutaneous injection, or intramuscular injection. A US28, IE1 and/or pp71 antagonist can be administered orally or rectally through appropriate formulation with carriers and excipients to form tablets, pills, capsules, liquids, gels, syrups, slurries, suspensions and the like. A US28, IE1 and/or pp71 antagonist can be administered topically, such as by skin patch, to achieve consistent systemic levels of active agent. A US28, IE1 and/or pp71 antagonist is formulated into topical creams, skin or mucosal patch, liquids or gels suitable to topical application to skin or mucosal membrane surfaces. A US28, IE1 and/or pp71 antagonist can be administered by inhaler to the respiratory tract for local or systemic treatment of CMV infection.

The dosage of the US28, IE1 and/or pp71 antagonist suitable for use with the methods of the disclosure can be determined by those skilled in the art from this disclosure. The US28, IE1 and/or pp71 antagonist will contain an effective dosage (depending upon the route of administration and pharmacokinetics of the active agent) of the US28, IE1 and/or pp71 antagonist and suitable pharmaceutical carriers and excipients, which are suitable for the particular route of administration of the formulation (i.e., oral, parenteral, topical or by inhalation). The active US28, IE1 and/or pp71 antagonist is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the active US28, IE1 and/or pp71 antagonist in water-soluble form. Additionally, suspensions of the active US28, IE1 and/or pp71 antagonist may be prepared as oily injection suspensions. Suitable lipophilic solvents or vehicles include fatty oils such as sesame oil, or synthetic fatty acid ester, such as ethyl oleate or triglycerides, or liposomes. Aqueous injection suspensions may contain substances, which increase the viscosity of the suspension, such as sodium carboxymethyl cellulose, sorbitol, or dextran. The suspension may optionally contain stabilizers or agents to increase the solubility of the complex or combination to allow for more concentrated solutions.

A CMV related disease or disorder includes cancers (e.g., brain, prostate and colon cancers); congenital CMV infections, perinatal CMV infections, immunocompetent patient CMV infections, CMV mononucleosis, post-transfusion CMV infections, immunocompromised CMV infections, CMV pneumonitis, CMV GI disease and CMV retinitis.

Following infection, CMV typically remains in a latent state within the cells. In immunocompromised or immunosuppressed patients, CMV reactivation can result in invasive CMV disease such as pneumonitis, esophagitis, encephalitis, hepatitis, pancreatitis, adrenalitis, esophagitis, gastritis, enteritis, colitis, and retinitis.

Examples of cellular proliferative and/or differentiative disorders that can be treated by the methods and compositions of the disclosure include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as those affecting the lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine, cancer of the esophagus, and cancers of the brain including glioblastoma multiforme.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Exemplary immune disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. The diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Additional examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein are useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

In one embodiment, the disclosure provides a method of inhibiting a cell proliferative disorder or treating a cell proliferative disorder associated with a CMV infection. The method comprises inhibiting the activity or expression of a CMV gene product or gene, respectively, selected from the group consisting of IE1, US28 and pp71. Various agents can be used to effectuate the inhibition of activity or expression. For example, expression may be inhibited by using inhibitory nucleic acid molecules (e.g., antisense, ribozymes, siRNA and the like).

RNAi is a remarkably efficient process whereby double-stranded RNA (dsRNA) induces the sequence-specific degradation of homologous mRNA in animals and plant cells (Hutvagner and Zamore, Curr. Opin. Genet. Dev., 12:225-232, 2002; Sharp, Genes Dev. 15:485-490, 2001). In mammalian cells, RNAi can be triggered by 21-nucleotide (nt) duplexes of small interfering RNA (siRNA) (Chiu et al, Mol Cell 10:549-561, 2002; Elbashir et al., Nature 411:494-498, 2001), or by micro-RNAs (miRNA), functional small-hairpin RNA (shRNA), or other dsRNAs that are expressed in vivo using DNA templates with RNA polymerase III promoters (Zeng et al., Mol. Cell. 9:1327-1333, 2002; Paddison et al., Genes Dev. 16:948-958, 2002; Lee et al., Nature Biotechnol. 20:500-505, 2002; Paul et al., Nature Biotechnol. 20:505-508, 2002; Tuschl, Nature Biotechnol. 20:440-448, 2002; Yu et al. Proc. Natl. Acad. Sci. USA 99:6047-6052, 2002; McManus et al., RNA 8:842-850, 2002; Sui et al., Proc. Natl. Acad Sci. USA 99:5515-5520, 2002).

Suppliers of RNA synthesis reagents and synthesized RNA oligonucleotides include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

In one embodiment, the disclosure provides siRNA molecules, methods of making siRNA molecules and methods (e.g., research and/or therapeutic methods) for using siRNA molecules. The siRNA molecule can have a length from about 10-50 or more nucleotides (or nucleotide analogs), about 16-30 nucleotides (or nucleotide analogs), about 15-25 nucleotides (or nucleotide analogs), or about 20-23 nucleotides (or nucleotide analogs). The nucleic acid molecules or constructs of the invention include dsRNA molecules that have nucleotide (or nucleotide analog) lengths of about 10-20, 20-30, 30-40, 40-50, 15, 16, 17, 18, 19, 20, 21, 22, 23, 24, 25, 26, 27, 28, 29, 30 or more. In one embodiment, the siRNA molecule has a length of 21 nucleotides and comprise sequences that are substantially identical or capable of hybridizing to a sequence encoding a IE1, US28 or pp71 polypeptide. It is to be understood that all ranges and values encompassed in the above ranges are within the scope of the present invention. Long dsRNAs to date generally are less preferable as they have been found to induce cell self-destruction known as interferon response in human cells. siRNAs typically include 5' terminal phosphate (e.g., 5' $PO_4$) and a 3' short overhangs of about 2 nucleotides (e.g., 3'-deoxythymidines, e.g., 3' dTdT overhangs). The dsRNA molecules of the invention can be chemically synthesized, transcribed in vitro from a DNA template, or made in vivo from, for example, shRNA. In a preferred embodiment, the siRNA can be a short hairpin siRNA (shRNA). Even more preferably, the shRNA is an expressed shRNA. In another embodiment, the siRNA can be associated with one or more proteins in an siRNA complex.

The siRNA molecules of the disclosure include a sequence that is sequence sufficiently complementary to a portion of the viral (e.g., CMV, e.g., HCMV) genome to mediate RNA interference (RNAi), as defined herein, i.e., the siRNA has a sequence sufficiently specific to trigger the degradation of the target RNA by the RNAi machinery or process. The siRNA molecule can be designed such that every residue of the antisense strand is complementary to a residue in the target molecule. Alternatively, substitutions can be made within the molecule to increase stability and/or enhance processing activity of said molecule. Substitutions can be made within the strand or can be made to residues at the ends of the strand.

The target RNA cleavage reaction guided by siRNAs is highly sequence specific. In general, siRNAs containing nucleotide sequences substantially complementary to a portion of the target gene, e.g., target region of an HCMV mRNA, are typically used for inhibition. However, 100% sequence identity between the siRNA and the target gene is not required to practice the methods of the disclosure. Thus the disclosure has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition as shown in the examples. Alternatively, siRNA sequences with nucleotide analog substitutions or insertions can be effective for inhibition. For example the first and second strands can be about 80% (e.g., 85%, 90%, 95%, or 100%) complementary to a target region of HCMV mRNA (e.g., the sequence of a strand of the dsRNA and the sequence of the target can differ by 0, 1, 2, or 3 nucleotide(s)).

Moreover, not all positions of a siRNA contribute equally to target recognition. Mismatches in the center of the siRNA are most critical and can essentially abolish target RNA cleavage. In contrast, the 3' nucleotides of the siRNA typically do not contribute significantly to specificity of the target recognition. In particular, 3' residues of the siRNA sequence which are complementary to the target RNA (e.g., the guide sequence) generally are not critical for target RNA cleavage.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions.times.100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A useful, non-limiting example of a local alignment algorithm utilized for the comparison of sequences is the algorithm of Karlin & Altschul, Proc. Natl. Acad Sci. USA 87:2264-68 (1990), modified as in Karlin & Altschul, Proc. Natl. Acad. Sci. USA 90:5873-77 (1993). Such an algorithm is incorporated into the BLAST programs (version 2.0) of Altschul, et al., J. Mol. Biol. 215: 403-10 (1990).

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul, et al., Nucleic Acids Res. 25(17):3389-3402 (1997). In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the siRNA and the portion of the target gene is typically used. For example, in the context of an siRNA of about 19-25 nucleotides, e.g., at least 15-21 identical nucleotides are preferred, more preferably at least 17-22 identical nucleotides, and even more preferably at least 18-23 or 19-24 identical nucleotides. Alternatively worded, in an siRNA of about 19-25 nucleotides in length, siRNAs having no greater than about 5 mismatches are preferred, preferably no greater than 4 mismatches are preferred, preferably no greater than 3 mismatches, more preferably no greater than 2 mismatches, and even more preferably no greater than 1 mismatch.

Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6 (log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., et al., 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel, et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

In one embodiment, the RNA molecules of the disclosure are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

In another embodiment of the disclosure the RNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, NH$_2$, NHR, NR$_2$ or ON, wherein R is C$_1$-C$_6$ alkyl, alkenyl or alkynyl and halo is F, Cl, Br or I.

Also useful are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Crosslinking can be employed to alter the pharmacokinetics of the composition, for example, to increase half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions of the disclosure can be unconjugated or can be conjugated to another moiety, such as a nanoparticle, to enhance a property of the compositions, for example, a pharmacokinetic parameter such as absorption, efficacy, bioavailability, and/or half-life. The conjugation can be accomplished by methods known in the art, for example, using the methods of Lambert et al. (2001), Drug Deliv. Rev., 47(1), 99-112 (describes nucleic acids loaded to polyalkylcyanoacrylate (PACA) nanoparticles); Fattal et al., J Control Release 53:137-143, 1998 (describes nucleic acids bound to nanoparticles); Schwab et al., Ann. Oncol., 5 Suppl. 4:55-8, 1994 (describes nucleic acids linked to intercalating agents, hydrophobic groups, polycations or PACA nanoparticles); and Godard et al., Eur. J. Biochem., 232:404410. 1995 (describes nucleic acids linked to nanoparticles).

The nucleic acid molecules of the disclosure can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, for example, using $^3$H, $^{32}$P, or other appropriate isotope.

The ability of the siRNAs of the present invention to mediate RNAi is particularly advantageous considering the rapid mutation rate of viruses. The invention contemplates several embodiments which further leverage this ability by, e.g., targeting a region of the CMV genome that is present in an mRNA that encodes more than one protein. This approach provides the advantage that it allows inhibition of two or more proteins with a single RNAi agent. A second important advantage is that it much less likely that an escape mutant will appear in a region of genomic sequence from which multiple proteins are derived than in a region that encodes a single protein. In an exemplary embodiment, exon 3 of the UL123 and UL122 HCMV genes is targeted, as discussed in greater detail below. Additionally or alternatively, a subject's infected cells can be procured and the genome of the CMV virus within it sequenced or otherwise analyzed to synthesize one or more corresponding RNAi agents, e.g, siRNAs, shRNAs, or plasmids or transgenes expressing siRNAs. Additionally or alternatively, high mutation rates can be addressed by introducing several siRNAs that target different and/or staggered regions of the CMV genome.

Molecules that can be used as "negative controls" will be known to one of ordinary skill in the art. For example, a negative control siRNA can have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing a sufficient number of base mismatches into the sequence to limit sequence complementarity (e.g., more than about 4, 5, 6, 7 or more base mismatches).

In one embodiment, siRNAs are synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNA. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNA from a recombinant construct may be produced by introducing the construct into a zygote, an embryonic stem cell, or another multipotent cell derived from the appropriate organism.

In addition, not only can an siRNA of the invention be used to inhibit expression of more than one protein within the cell, but the siRNAs can be replicated and amplified within a cell by the host cell's enzymes. Alberts, et al., The Cell 452 (4th Ed. 2002). Thus, a cell and its progeny can continue to carry out RNAi even after the CMV RNA has been degraded.

RNA may be produced enzymatically or by partial/total organic synthesis, any modified ribonucleotide can be introduced by in vitro enzymatic or organic synthesis. In one embodiment, a siRNA is prepared chemically. Methods of synthesizing RNA molecules are known in the art, in particular, the chemical synthesis methods as described in Verna and Eckstein, Annul Rev. Biochem. 67:99-134 (1998). In another embodiment, a siRNA is prepared enzymatically. For example, a siRNA can be prepared by enzymatic processing of a long dsRNA having sufficient complementarity to the desired target RNA. Processing of long dsRNA can be accomplished in vitro, for example, using appropriate cellular lysates and ds-siRNAs can be subsequently purified by gel electrophoresis or gel filtration. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing.

The siRNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan & Uhlenbeck, Methods Enzymol. 180:51-62 (1989)). The RNA may be dried for storage or dissolved in an aqueous solution. The solution may contain buffers or salts to inhibit annealing, and/or promote stabilization of the single strands.

Another aspect of the disclosure includes a vector that expresses one or more siRNAs that include sequences sufficiently complementary to a portion of the CMV (e.g., HCMV) genome to mediate RNAi. The vector can be administered in vivo to thereby initiate RNAi therapeutically or prophylactically by expression of one or more copies of the siRNAs.

In one embodiment, synthetic shRNA is expressed in a plasmid vector. In another, the plasmid is replicated in vivo. In another embodiment, the vector can be a viral vector, e.g., a retroviral vector. Use of vectors and plasmids are advantageous because the vectors can be more stable than synthetic siRNAs and thus effect long-term expression of the siRNAs.

Viral genomes mutate rapidly and a mismatch of even one nucleotide can, in some instances, impede RNAi. Accordingly, also within the scope of the disclosure is a vector that expresses a plurality of siRNAs to increase the probability of sufficient homology to mediate RNAi or a plurality of siRNA to multiple targets. For example, these siRNAs can include two or more targets selected from the group consisting of IE1, US28 and pp71. In one embodiment, one or more of the siRNAs expressed by the vector is a shRNA. The siRNAs can be staggered along one portion of the CMV (e.g., HCMV) genome or target different genes in the CMV (e.g., HCMV) genome. In one embodiment, the vector encodes about 3 siRNAs, (e.g., about 5 siRNAS). The siRNAs can be targeted to conserved regions of the CMV (e.g., HCMV) genome.

An "antisense" nucleic acid can include a nucleotide sequence that is complementary to a "sense" nucleic acid encoding a protein, for example, complementary to the coding strand of a double-stranded cDNA molecule or complementary to an mRNA sequence. The antisense nucleic acid can be complementary to an entire coding stand of a viral, e.g., CMV (e.g., HCMV), gene, or to only a portion thereof.

An antisense nucleic acid can be designed such that it is complementary to the entire coding region of a viral, e.g., HCMV, mRNA, but more preferably is an oligonucleotide that is antisense to only a portion of the coding or noncoding region of a viral, e.g., HCMV, mRNA. For example, the antisense oligonucleotide can be complementary to the region surrounding the translation start site of a viral, e.g., HCMV, mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the disclosure can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are typically administered to a subject (e.g., by direct injection at a tissue site), or generated in situ such that they hybridize with or bind to cellular mRNA and/or genomic DNA encoding a viral gene, e.g., an HCMV gene, e.g., to IE1, US28 or pp71, to thereby inhibit expression of these proteins, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the disclosure is an α-anomeric nucleic acid molecule. An α-anomeric nucleic acid molecule forms specific double-stranded hybrids with complementary RNA in which, contrary to the usual β-units, the strands run parallel to each other (Gaultier et al, Nucleic Acids. Res. 15:6625-6641, 1987). The antisense nucleic acid molecule can also comprise a 2'-o-methylribonucleotide (Inoue et al., Nucleic Acids Res. 15:6131-6148, 1987) or a chimeric RNA-DNA analogue (Inoue et al. FEBS Lett., 215:327-330, 1987).

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a viral gene, e.g., a CMV gene, e.g., a IE1, US28 or pp71-encoding nucleic acid, can include one or more sequences complementary to, for example, the nucleotide sequence of IE1, US28 or pp71, and a sequence having known catalytic sequence responsible for mRNA cleavage (see U.S. Pat. No. 5,093,246 or Haselhoff and Gerlach (1988) Nature 334:585-591).

Agents of the disclosure can be administered alone or in combination to achieve the desired therapeutic result. The disclosure also contemplates administration with other agents, e.g., antiviral agents, to achieve the desired therapeutic result.

Physical methods of introducing the agents of the disclosure (e.g., siRNAs, vectors, or transgenes) include injection of a solution containing the agent, bombardment by particles covered by the agent, soaking the cell or organism in a solution of the agent, or electroporation of cell membranes in the presence of the agent. A viral construct packaged into a viral particle would accomplish both efficient introduction of an expression construct into the cell and transcription of RNA, including siRNAs, encoded by the expression construct. Other methods known in the art for introducing nucleic acids to cells may be used, such as lipid-mediated carrier transport, chemical-mediated transport, such as calcium phosphate, and the like. Thus the siRNA may be introduced along with components that perform one or more of the following activities: enhance siRNA uptake by the cell, inhibit annealing of single strands, stabilize the single strands, or otherwise increase inhibition of the target gene.

The agents may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the agent may be introduced.

Cells may be infected with CMV (e.g., HCMV) prior to, simultaneously with or following delivery of the agent. The cells may be derived from or contained in any organism. The cell may be from the germ line, somatic, totipotent or pluripotent, dividing or non-dividing, parenchyma or epithelium, immortalized or transformed, or the like. The cell may be a stem cell, e.g., a hematopoietic stem cell, cancer stem cell, neuronal stem cell, or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 30%, 40%, 50%, 60%, 70%, 80%, 90%, 95% or 99% or more of targeted cells is exemplary. Inhibition of gene expression refers to the absence (or observable decrease) in the level of viral protein, RNA, and/or DNA or gene product production. Specificity refers to the ability to inhibit the target gene without manifesting effects on other genes, particularly those of the host cell. The consequences of inhibition can be confirmed by examination of the outward properties of the cell or organism or by biochemical techniques such as RNA solution hybridization, nuclease protection, Northern hybridization, reverse transcription gene expression monitoring with a microarray, antibody binding, enzyme linked immunosorbent assay (ELISA), integration assay, Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT); green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the disclosure. Lower doses of injected material and longer times after administration of siRNA may result in inhibition in a smaller fraction of cells (e.g., at least 10%, 20%, 50%, 75%, 90%, or 95% of targeted cells).

Quantitation of gene expression in a cell may show similar amounts of inhibition at the level of accumulation of target RNA or translation of target protein. As an example, the efficiency of inhibition may be determined by assessing the amount of gene product (e.g., IE1, US28 and/or pp71 protein) in the cell; RNA may be detected with a hybridization probe having a nucleotide sequence outside the region used for the inhibitory double-stranded RNA, or translated polypeptide may be detected with an antibody raised against the polypeptide sequence of that region.

The siRNA may be introduced in an amount that allows delivery of at least one copy per cell. Higher doses (e.g., at least 5, 10, 100, 500 or 1000 copies per cell) of material may yield more effective inhibition; lower doses may also be useful for specific applications.

In addition, other therapies may be combined with the agents described above. Such therapies can include agents the prevent further spread or infection. For example, various tyrosine kinase small molecule inhibitors and peptidomimetics can also be used in the methods and compositions of the disclosure. A number of tyrosine kinase inhibitors useful in the disclosure can be identified by one of skill in the art. For example, AZD2171; Dasatinib; Erlotinib; Gefitinib; Imatinib; Lapatinib; Nilotinib; Semaxanib; SGI-AXL-277 (a pyrrolopyrimidine) (SuperGen); Sunitinib; and Vandetanib. Other examples of tyrosine kinase inhibitors include: imatinib mesylate (Gleevec®) marketed by Novartis, IMC-3G3 (anti-PDGFR-α monoclonal antibody) developed by ImClone, sunitinib malate (Sutent®) developed by Pfizer, sorafenib tosylate (Nexavar®) marketed by Bayer, and Vatalanib (PTK787/ZK222584). In addition, Leflunomide (Arava®) is a small-molecule PDGFR tyrosine kinase inhibitor, and AG013736 (Axitinib®) by Pfizer is an imidazole derivative that inhibits the tyrosine kinase portion of all VEGFRs and PDGFR-B. Axitinib (also known as AG013736; N-Methyl-2-[[3-[(E)-2-pyridin-2-ylethenyl]-1H-indazol-6-yl]sulfanyl]benzamide) is a small molecule tyrosine kinase inhibitor under development by Pfizer. Bosutinib (rINN/USAN; code named SKI-606; 4-[(2,4-dichloro-5-methoxyphenyl)amino]-6-methoxy-7-[3-(4-methylpiperazin-1-yl)propoxy]quinoline-3-carbonitrile) is a tyrosine kinase inhibitor being developed by Wyeth. Cediranib (tentative trade name Recentin; 4-[(4-fluoro-2-methyl-1H-indol-5-yl)oxy]-6-methoxy-7-[3-(pyrrolidin-1-yl)propoxy]quinazoline), also known as AZD2171, is a potent inhibitor of vascular endothelial growth factor (VEGF) receptor tyrosine kinases. Dasatinib, also known as BMS-354825 (N-(2-chloro-6-methylphenyl)-2-[[6-[4-(2-hydroxyethyl)-1-piperazinyl]-2-methyl-4-pyrimidinyl]amino]-5-thiazole carboxamide monohydrate), is a drug produced by Bristol-Myers Squibb and sold under the trade name Sprycel®. Dasatinib is an oral dual BCR/ABL and Src family tyrosine kinases inhibitor. Erlotinib hydrochloride (originally coded as OSI-774; N-(3-ethynylphenyl)-6,7-bis(2-methoxyethoxy)quinazolin-4-amine) is marketed in the United States by Genentech and OSI Pharmaceuticals and elsewhere by Roche under the tradename Tarceva®. Gefitinib (INN) (originally coded ZD1839; N-(3-chloro-4-fluoro-phenyl)-7-methoxy-6-(3-morpholin-4-ylpropoxy)quinazolin-4-amine is similar manner to erlotinib (marketed as Tarceva®). Gefitinib is marketed by AstraZeneca and Teva under the trade name Iressa®. Imatinib is currently marketed by Novartis as Gleevece® (USA) or Glivec® (Europe/Australia) as its mesylate salt, imatinib mesilate (INN). It was originally coded during development as CGP57148B or STI-571 (4-[(4-methylpiperazin-1-yl)methyl]-N-[4-methyl-3-[(4-pyridin-3-ylpyrimidin-2-yl)amino]-phenyl]-benzamide). Lapatinib (INN) or lapatinib ditosylate (USAN), also known as GW572016 (N-[3-chloro-4-[(3-fluorophenyl)methoxy]phenyl]-6-[5-[(2-methylsulfonylethylamino)methyl]-2-furyl]quinazolin-4-amine), is marketed by GSK under the tradename Tykerb® and Tyverb®. Lestaurtinib (rINN, codenamed CEP-701) is a tyrosine kinase inhibitor. Nilotinib, in the form of the hydrochloride monohydrate salt, is a tyrosine kinase inhibitor, also known by its clinical code AMN107 (4-methyl-N-[3-(4-methylimidazol-1-yl)-5-(trifluoromethyl)phenyl]-3-[(4-pyridin-3-ylpyrimidin-2-yl)amino]benzamide). Semaxanib (SU5416; (3Z)-3-[(3,5-dimethyl-1H-pyrrol-2-yl)methylidene]-1H-indol-2-one) is a tyrosine kinase inhibitor. Sorafenib tosylate (Nexavar®) marketed by Bayer. Sunitinib (marketed as Sutent®, and previously known as SU11248; N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide) is an oral, small-molecule, multi-targeted receptor tyrosine kinase (RTK) inhibitor. Vandetanib (also known as ZD6474; N-(4-bromo-2-fluoro-phenyl)-6-methoxy-7-[(1-methyl-4-piperidyl)methoxy]quinazolin-4-amine), is a tyrosine kinase inhibitor currently undergoing clinical trials. Vandetanib is being developed by AstraZeneca. Vatalanib (PTK787/ZK222584) a protein tyrosine kinase inhibitor being developed by Bayer. In addition, Leflunomide (Arava®) is a small-molecule PDGFR tyrosine kinase inhibitor; AZD2171; and SGI-AXL-277 (a pyrrolopyrimidine).

Compositions comprising one or more of the foregoing inhibitors are useful in treating CMV related diseases and disorders. For example, in one embodiment, a pharmaceutical composition comprising a tyrosine kinase inhibitor is useful for inhibiting or reducing the infection of or spread of a CMV. In yet another embodiment, a pharmaceutical composition comprising an antibody that binds to and inhibits the interaction of a PDGFR-alpha with its ligand is used. In yet another embodiment, an antisense or siRNA molecule can be used to reduce the expression of a PDGFR-alpha polypeptide. In yet a further embodiment, a combination of any of the foregoing can be used.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, intravitreal, intracerebral, spinal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active agent/compound (e.g., a protein or anti-PDGF antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The active agent/compound can be formulated for intravitreal administration. Such formulation can comprise slow release devices and materials (e.g., silicon or silicon oxide material). Such formulations are useful for the treatment of retinitis. In some embodiment, the active agent as described herein can be used in combination with other retinitis therapies (e.g., Vitravene® (fomivirsen)—an antisense drug to treat cytomegalovirus (CMV) retinitis in people with AIDS; developed by Isis and marketed by Novartis).

In one embodiment, the active compounds are prepared with carriers that will protect the compound/agents against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Slow release materials can also be obtained commercially from Alza Corporation and Nova Pharmaceuticals, Inc. Liposomal suspensions (including liposomes targeted to infected cells with monoclonal antibodies to surface (cell or viral) antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD$_{50}$ (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED$_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC$_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical compositions can be included in a container, pack, or dispenser together with instructions for administration.

The effectiveness, infectivity or treatment of a subject can be measured by commonly used techniques. For example, standard techniques used for determining CMV infection include those identified below. Accordingly, the usefulness and efficacy of an agent used for the treatment of or prevention of CMV infection can be measured. Conventional viral cultures of tissue biopsy or body fluid (e.g., buffy coat (WBCs), plasma, urine, respiratory secretions, or stool) can be used to measure infectivity. The specimen is incubated with fibroblasts at 36° C. for 1-3 weeks, and the fibroblasts are then examined under the microscope for cytopathic changes. The identification of cytomegalic inclusion bodies is used for the diagnosis of CMV disease or disorder. In another aspect, the shell vial culture technique in which the specimen is placed onto the fibroblast monolayer and centrifuged to help the virus penetrate the fibroblast, increases the viral yield 4-fold. The monolayer is stained 24-48 hrs later using monoclonal antibodies against a CMV protein produced during the immediate early phase of viral replication. In yet another aspect, the PP-65 antigenemia test is used wherein specific monoclonal antibodies are used to detect, in PMN leukocytes, a CMV matrix phosphoprotein known as pp-65. In a further aspect, CMV DNA is PCR amplified and detected. The PCR method is used either qualitatively (diagnostic PCR) or quantitatively to measure the viral load, which is proportional to the level of CMV DNA. CMV Serology Anti-CMV antibody (IgG and IgM) titers are routinely measured in both donor and recipient, primarily for the purpose of assessing the patient's risk for future development of CMV disease or disorder.

The following examples are offered to more fully illustrate the disclosure, but are not to be construed as limiting the scope thereof.

EXAMPLES

Glioblastoma and Neural Precursors Primary Cultures

Primary glioblastoma cultures were generated using tissue from surgical resections at CPMC obtained according to the IRB approved protocol. Tissues were dissociated using enzymatic and mechanical dissociation. CD133 and SSEA1 positive and negative fractions were obtained by magnetic activated cell sorting (MACS), using the autoMACS Pro Separator in conjunction with cell separation reagents from Miltenyi Biotec (kit #130-050-801 for CD133 and #130-094-530 for SSEA1). Single cell suspensions were cultured using neural basal medium+N2 supplement, 20 ng/ml EGF, 20 ng/ml bFGF, and 1 µg/ml laminin. The NPC cell line was derived from the hippocampus tissue removed from a patient with intractable epilepsy. Cells were characterized by immunofluorescence and found positive for Nestin, GFAP, Tuj1, and Olig 2. All experiments were performed on passages 2-5 from the NPC culture. U87 glioma HEL cell lines were obtained from ATCC and maintained in DMEM+10% FBS.

Glioma Neurosphere (Tumor-Sphere) Assays.

Tumor sphere assays were used to measure self-renewal potential of the glioma neurospheres. CD133+ sorted primary human GBM cells were initially seeded in complete neurosphere growth media at low density (300 cells/ml), so that individual cells could form spatially distinct spheres. Control and IE1 siRNA were added to glioma spheres in triplicate wells 24 h following initial culturing. Monitoring the growth of primary spheres (a sphere is composed of approximately 50 cells) was performed daily by microscopic examination. 72-96 h following siRNA treatment primary glioma spheres were photographed and counted. Neurospheres were next dissociated and passaged through a sterile filter to obtain single cell suspensions which were cultured at low density, and allowed to form secondary (2°) neurospheres for an additional 72 h.

Taqman for HCMV Gene Products.

Quantitative TaqMan analysis of primary sorted cell fractions, 118.5 ng of GBM 177 RNA and 127.5 ng of GBM 790 were reverse transcribed. cDNA was then analyzed in duplicate using TaqMan FAST universal PCR master mix (Applied Biosystems) with the following primers and probes: IE1 F-5'-AAGCGGCCTCTGATAACCAAG-3' (SEQ ID NO:1), R-5'-GAGCAGACTCTCAGAGGATCG-3' (SEQ ID NO:2), probe-Fam CATGCAGATCTCCTCAATGCGGCG-Tamra (SEQ ID NO:3); Human GAPDH TaqMan primers/probe #HS02786624-g1 (Applied Biosystems). Standard curves were generated with 5-fold serial dilutions of either purified Ad169 viral DNA (Advanced Biotech) or TaqMan control human genomic DNA (Applied Biosystems), respectively. Gene copy number was then adjusted to copy number per µg of RNA input and IE1 expression was normalized to GAPDH.

siRNA Mediated IE1 Knockdown.

Initial experiments were performed with each siRNA individually and the two duplexes combined. As a negative control, non-targeting control pool from Dharmacon (D-001810-10-05) was used. After optimization, all subsequent IE1KD experiments used the combination of the two oligonucleotide duplexes listed below.

```
1-Sense:
                                         (SEQ ID NO: 4)
GGAAGGAGGUUAACAGUCAUU 1-Antisense:
                                         (SEQ ID NO: 5)
UGACUGUUAACCUCCUUCCUU 2-Sense:
                                         (SEQ ID NO: 6)
GGAAGAAAGUGAACAGAGUUU
```

```
-continued
2-Antisense:
                                          (SEQ ID NO: 7)
ACUCUGUUCACUUUCUUCCUU
```

Final concentrations of siRNA used were: 20 nM/duplex (40 nM total) to KD IE1 and 40 nM of non-targeting siRNA as control. Primary GBM cells (3 wells of a 6 well plate/condition) were incubated with siRNA (40 nM/well), Lipofectamine (4-6 μl/well) in 2 ml of neural basal media with growth factors, but no antibiotics. Effective protein knockdown was verified at 48-72 h post transfection and prior to functional assays.

Taqman Detection for microRNA 145.

Taqman MicroRNA assays # hsa-miR-145 and # RNU48 were purchased from Applied Biosystems. 20 ng RNA/sample was reverse transcribed using the Applied Biosystems TaqMan MicroRNA Reverse Transcription kit (PN 4366596) and further used in qPCR amplification, using the TaqMan Fast Universal PCR Mix #4352042, according to manufacturer's instructions. Each condition was run in quadruplicate and all experiments were repeated twice.

Micro RNA145 Knockdown.

Knockdown was accomplished using the Ambion Anti-miR Inhibitor AM 114880, targeting the mature miRNA sequence of human has-miR-145, GUCCAGUUUUC-CCAGGAAUCCCU (SEQ ID NO:8). The inhibitor was used at 30 nM final concentration, using the manufacturer's transfection protocol. miR-145 knockdown was measured by Taqman as explained above.

Expression Profiling Using the HCMV DNA Array.

Total RNA was processed for microarray hybridization at the Center for Applied Genomics, UMDNJ-New Jersey Medical School. The HCMV arrays were printed and processed. Briefly, the array contains 65-mer oligonucleotides representing 194 predicted open reading frames of the HCMV strain AD169, 19 oligonucleotides for ORFs in the Toledo strain that are not found in AD169 and 44 human genes as controls. Total RNA (3 μg) was reversed transcribed to cDNA using Superscript II RT in the presence of Cyanine-3 or Cyanine-5 dUTP. The labeled cDNA was purified and hybridized to the arrays at 58° C. for 16 hours. The slides were scanned using an Axon 4200AL scanner and the images were processed using GenePix Pro 6.1. A normalization factor was calculated using 36 human control genes by dividing the median intensity of the Cy5 signal by the median intensity of Cy3 signal of the controls. The data were normalized by multiplying the Cy3 signal of each spot by the normalization factor. The ratio of the Cy5 median intensity over the Cy3 median intensity was determined for each spot and the average ratio determined for the replicate spots.

Spontaneous Mouse Glioma Model

Balb/c mice were bred and handled according the Institutional Animal Care and Use Committee protocol. The intracerebral ventricular method of injection is known in the art. Postnatal day one mice were anesthetized using hypothermia and placed on a cooled stereotaxic neonatal frame. In vivo jetPEI™ (Polyplus™) mixed with plasmid DNA (700 ng total DNA) was injected at a flow rate of 0.4 μl/min into the right lateral ventricle. The following plasmids were utilized for glioma induction in equal parts: pT2/C-Luc/PGK-SB100, pT2/Cag-NrasV12, pT2/shP53/GFP4/mPDGF, and pT2/Cag-IE1 or pT2/C-Neo. Tumor development was monitored starting at three weeks of age by in vivo bioluminescence. At moribund stage, animals were anesthetized with a ketamine/xylazine cocktail and transcardially perfused with phosphate buffered solution followed by 4% paraformaldehyde. Brains were collected and post-fixed in 10% formalin. Alternatively, brains were collected without perfusion, snap frozen in a dry ice-ethanol bath, and shipped on dry ice.

Mouse Affymetrix Data Analysis.

Mouse RNA was profiled using MoGene-1_0-st-v1 high-density microarrays. Gene expressions were estimated by the RMA method implemented in aroma affymetrix. Log-gene expression ratios, calculated using the two controls as a reference, were then clustered by genes and samples. Clustering of the six tumor samples was done for autosomal chromosomes using hierarchical clustering (euclidean distance and Ward agglomeration). Bioinformatics analysis of the normalized Affymetrix datasets was performed using Ingenuity Pathways Analysis (Ingenuity Systems http: [//]www.ingenuity.com).

Immunofluorescence and Immunohistochemistry.

Primary cultures and NPCs were fixed using methanol (10 min, RT) and immunostained using the following primary antibodies (overnight incubation, 4C). CD133 antibody (1/100) Miltenyi Biotec (130-090-422), IE1 MAB810 Chemicon (1/100), Sox2 #26831 Epitomics (1/1000), PDG-FRα E2694 Spring Biosciences (1/100), i-NOS #06-573 (1/500), Integrin a6 (CD49f) # mab1378 (1/500), Bmi-1#05-637 (1/100) and Olig 2 #AB9610 (1/100) from Millipore, Tuj1 (Beta III Tubulin) #7808 (1/1000), CD31#9498 (1/1000), Aurora B#2254 (1/200), Ki-67#833 (1/1000), GFAP#7260 (1/500), Nestin #7659 (1/1000), EpCAM#68892 (1/1000), Oct4 #18976 (1/1000) all from AbCAM, BrdU sc20045 (1/1000) from Santa Cruz, STAT3 (Tyr705) #9131 (1/1000) from Cell Signaling. Fluorescently and HRP-labeled secondary antibodies were from Invitrogen. Nuclei were stained with DAPI or Propidium Iodide containing mounting medium from Vector Labs. For tissue immunohistochemistry, antigen retrieval (Citra Plus, HK080-5K, from Biogenex) and pepsin digestion were used. Following overnight incubation with primary antibodies, Biogenex' supersensitive Polymer HRP IHC detection system was used following the manufacturer's directions (QD400-60K). Counterstaining was done using Hematoxylin. Cells and tissues were visualized using a Nikon Eclipse C1-Confocal microscope (Nikon TE2000-U) fitted with a "Cool Snap" Photometrix camera (Roper Scientific). Images were acquired using EZ-C1 v2.20 software and further processed using Photoshop (Adobe Photoshop CS4).

Human Phoshpho-Kinase Array and Western Blot Assays.

Cell lysates were prepared in the lysis buffer provided within the Proteome profiler array kit for human pluripotent stem cell array (ARY010) and human apoptosis antibody array (ARY009) from R&D Systems. Parallel determination of the relative levels of protein phosphorylation was conducted according to the kit instructions, using 200 μg protein/sample. Western blot assays were carried out with antibodies listed above and the following additional primary antibodies Bax (D2E11) #5023 (1/500), phosphor-p53 sampler kit #9919 (1/500), Cleaved Caspase 3 (Asp175) #9961 from Cell Signaling; Actin# A2066 (1/1000) from Sigma, and TOP2A antibody (1/1000) MAB 6540 from R&D Systems. Secondary antibodies and detection systems were used.

Viruses.

Towne, and TB40-GFP HCMV strains were obtained from ATCC and grown in human embryonic fibroblasts (HEL). The TR virus strain was a gift from Dr. Lee Fortunato, University of Idaho. IE1 overexpression in primary HCMV negative human GBM or NPC cells was achieved using retroviral transduction.

Tissue RNA and Protein Extraction.

Brain tissue was lysed and homogenized in 1 mL Qiazol (Qiagen) using a TissueRuptor probe (Qiagen) and Qiashredder column (Qiagen). 200 uL of chloroform was added to the homogenized lysate, vortexed, and centrifuged for 15 minutes at 9500 rpms. RNA was then extracted from the upper aqueous fraction using the RNeasy lipid tissue mini kit (Qiagen) according to the manufacturer's instructions. The integrity of the RNA was verified by spectroscopy with a nanodrop 2000 and electrophoresis on a 1% agarose gel. 300 uL of 100% ethanol was added to the remaining interphase and organic phase, incubated at room temperature for 3 minutes, and centrifuged for 5 minutes at 4000 rpms to pellet the precipitated DNA. The protein-containing supernatant was then moved to a fresh microfuge tube and precipitated with 500 uL isopropanol for 10 minutes at room temperature. The protein was pelleted by centrifugation at 9500 rpms for 10 minutes, and then rinsed 3 times with 1 mL 0.3M guanidine HCL in 95% ethanol followed by centrifugation for 5 minutes at 7500 rpms. The pellet was rinsed once with 100% ethanol, allowed to dry, and resuspended in 1% SDS. To facilitate solubilization, the protein was incubated at 50 degrees for 20 minutes then centrifuged for 10 minutes at 8500 rpms to pellet the insoluble protein fraction.

RT-PCR for HCMV Gene Products.

1 ug of total RNA was reverse transcribed into cDNA using the iScript cDNA synthesis kit (BioRad) according to the manufacturer's instructions. Standard end-point PCR was then performed using the Taq PCR Core kit (Qiagen) with an input of 1 uL of cDNA for each experimental sample, water only for the negative control, and 1 uL of cDNA from CMV infected cells for the positive control.

RT-PCR Detection of HCMV Gene Products.

The primers used for PCR analysis are as follows: IE1 F-5'-AGCACCATCCTCCTCTTCCTCTG-3' (SEQ ID NO:9), R-5'-AAGCGGCCTCTGATAACCAAGCC-3' (SEQ ID NO:10); Rab14 F-5'-GCAGATTTGGGATACAGCAGG-3' (SEQ ID NO:19), R-5'-CAGTGTTTGGATTGGT-GAGATTC-3' (SEQ ID NO:11). The PCR amplification cycle was repeated 50 times with a 60° C. annealing temperature for the IE1 primers and a 58° C. annealing temperature for the Rab14 primers. 20 uL of each 50 uL PCR reaction was resolved on a 1% agarose gel and the size of each amplicon (IE1=299 base pairs, Rab14=167 base pairs) was verified relative to a 1 KB DNA ladder (Fermentas). The DNA from the remainder of each PCR reaction was then isolated using the MinElute PCR Purification kit (Qiagen) and sequenced.

Cellular Fractionation of Primary Glioma Tissue.

Whole brain tissue was homogenized in 1 mL cold PBS containing protease inhibitors using a TissueRuptor probe (Qiagen). Cells were pelleted by centrifugation and rinsed once in 1 mL cold PBS containing protease inhibitors. Cell fractions were then prepared using a Subcellular Protein Fractionation Kit (Pierce) according to the manufacturer's instructions. Equivalent amounts of protein from each fraction were then resolved on a 4-12% Bis-Tris SDS-PAGE gel (BioRad), transferred to a PVDF membrane, and blotted with antibodies to IE1 (Mab810, Millipore), PDGFRalpha (Spring Biosciences), Sox2 (Epitomics), and GAPDH (MAB374, Millipore).

Differentiation Assays.

GSCs treated with control and IE1 siRNA (48 h) were cultured on laminin coated chamber slides and bFGF and EGF withdrawn from the proliferative media. Cultures were divided in two groups of differentiating conditions, one set of cultures exposed to 2% FBS (to promote glial differentiation) and another set to retinoic acid (500 nM final concentration, added every other day) to promote neuronal differentiation. Cultures were fixed and evaluated by immunofluorescence 7 days following culturing in differentiating conditions. Tuj1, GFAP, Nestin, and Olig 2 antibodies were used as described above. Cells positive for all afore mentioned markers per 400 cells for each condition, were counted. Student t-Test was used to determine statistical significance between control/IE1 siRNA treated cultures. The experiment was repeated twice for two GSCs.

Cell Cycle and Apoptosis Assays Using Flow Cytometry Analysis.

The APO-BrdU Kit (#556405) from BD Pharmingen was used to detect the percentage of apoptotic cells in IE1KD and control treated glioma cultures. The kit is a two color staining method for simultaneous labeling of DNA breaks and total cellular DNA, to determine the percentage of apoptotic cells within a general cell population. Cells were fixed in 70% ethanol and labeled according to the manufacturer's instructions. Analysis was run using flow cytometry as described below. Each experiment was repeated twice. For the analysis of the apoptotic cells or cells in S-phase, subconfluent glioma cells targeted with control or IE1 siRNA for 72 h were pulsed with 10 µmol/L BrdU (Sigma) for 120 minutes prior to harvesting and fixation in 70% ethanol. Cells were subsequently denatured in 2 mol/L HCl and stained with anti-BrdU monoclonal antibody (Santa Cruz Biotechnology, Santa Cruz, Calif.) followed by FITC-conjugated secondary anti-mouse IgG (Molecular Probes/Invitrogen). After counter-staining with propidium iodide solution (10 µmol/L) cells were analyzed by flow cytometry.

Intracranial Xenografts of Primary Human GSC Cultures.

After short term culture, neurospheres from primary GSC cultures were centrifuged for 5 minutes at 10000 rpm and resuspended as a single cell suspension in serum-free Neurobasal Media (Invitrogen #21103-049). 50,000 cells in 4 µL were stereotaxically implanted into the right frontal lobe of athymic BALB/c nu/nu mice under an approved Institutional Animal Care and Use Committee protocol. Briefly, mice were anesthetized with ketamine (80 mg/kg), xylazine (5 mg/kg) and isoflourane, and placed on a stereotaxic device using ear bars. The scalp was cleaned with Betadine, and an incision made over the middle frontal bone. Using an 18 gauge needle, a hole was made through the skull 2 mm right of midline and 2 mm behind bregma. A syringe attached to the stereotaxic device is lowered to a depth of 3 mm, and the cell suspension is injected slowly into the frontal lobe. The scalp is cleaned and sealed, and a stitch is placed to close the opening. Mice were monitored and maintained for five weeks, or until the development of neurologic symptoms, or greater than 15% weight loss. Brains of euthanized mice were collected, fixed in formalin, paraffin embedded, and sectioned. Slides were stained with Hematoxlyin and Eosin, and then scanned using the Mirax MIDI whole slide high resolution scanning system (Carl Zeiss MicroImaging, Jena, Germany). The digitization of slides was controlled using an Allied Vision Marlin CCD Camera (Allied Vision Technologies GmbH, Germany) with a Zeiss Plan-Apopchromat 20× objective (Carl Zeiss Optronics, GmbH, Germany) to generate images at a resolution of 0.32 microns/pixel.

Expression Profiling Using Human Gene ST1 and Mouse Affymetrix Arrays.

Affymetrix Human Gene 1.0 ST arrays were processed according to the Affymetrix Expression Analysis Whole Transcript (WT) Sense Target Labeling Protocol (Affymetrix Inc., Santa Clara, Calif.). Briefly, total RNA (300 ng) was converted to double strand cDNA. cRNA was obtained by an in vitro transcription reaction and used as the template for generating a new 1st strand cDNA. The cDNA was fragmented, end-labeled with biotin and hybridized to the Array for 16 hours at 45° C. using the GeneChip Hybridization Oven 640. Washing and staining with Streptavidin-phycoerythrin was performed using the GeneChip Fluidics Station 450 and the images acquired using the Affymetrix Scanner 3000 7G Plus. The data was normalized using quantile normalization with the RMA algorithm32 for gene-level intensities and the ratio determined for each gene using Partek Genomics Suite (Partek Inc St. Louis, Mo.). Total RNA was processed at the microarray facility from the center for applied genomics at Public Health Research Institute in New Jersey, using the Affymetrix Gene ST.1. Mouse RNA was assayed on Affymetrix MoGene-1_0-st-v1 high-density microarrays and analyzed as described in the main Methods section.

Human Affymetrix Data Analysis.

Mean values of selected human and HCMV transcripts in the IE1 KD vs Control are displayed using the R program heatmap.2 from the package 'gplots'. The package is available from the R repository CRAN, and is maintained by Gregory R. Warnes.

Statistical Analysis

Statistical analyses were performed using student T-test, where appropriate, as indicated. Statistical analysis of microarray (SAM) was used to analyze results from HCMV, human, and mouse DNA arrays.

IE1 mRNA and protein expression was observed in over 75% of a collection of ~40 human primary glioma cells and tissues (FIG. 1A-B), excluding the possibility of laboratory HCMV contaminants. Double immunofluorescence of GBM tissues showed co-localization of CD133 (a GSC marker) and IE1 in situ (FIG. 1, c-e). CD133+ sorted GBM cells grown as tumor spheres demonstrated co-localization of IE1 with Nestin, another GSC marker (FIG. 1f). Since functional definition of GSCs includes the presence of multiple markers, additional analysis was performed and found that IE1 co-localized with PDGFRα, Integrin α6, i-Nos, Sox2 (FIG. 1g-k), and Olig2. GSCs used in this study were confirmed to initiate tumor growth in vivo. Comparative assessment of CD133– and CD133+ primary GBM cells (passage 0) showed IE1 mRNA and protein expression only in the CD133+ cell fraction, even when overall IE1 levels in whole tissue were below detection limit (FIG. 11, n-o). Primary GBM cells sorted using an alternate GSC marker—SSEA1-showed 2.1-5.9 fold enrichment for IE1 mRNA in the SSEA1+ fraction (Taqman, FIG. 1m).

Given the strong association between HCMV IE1 and GSC markers, it was hypothesized that IE1 may play a role in the maintenance of the stem-like phenotype. To assess the effects on IE1 expression on GSC self-renewal, a combination of two siRNA duplexes were used to knock down IE1 in endogenously infected tumor spheres. The term IE1siRNA designates the use of two combined siRNAs in all subsequent experiments. IE1KD caused significant reduction in the number of spheres and viable tumor cells (FIG. 2a). Self-renewal assays showed that IE1KD inhibited both primary and secondary neurosphere growth by ~50-60% (FIG. 2b). "Gain of function" studies showed that HCMV infection induced GSC self-renewal and expression of sternness markers in HCMV negative tumor spheres. IE1KD-mediated inhibition of this effect was specific, since it did not affect the growth of uninfected GSCs.

The mechanism underlying IE1 regulation of GSC self-renewal was investigated by screening a human stem cell antibody array. IE1KD inhibited expression levels of several stem cell markers (FIG. 2c). In particular, significant suppression of Sox2, an essential regulator of glioma initiation and growth, was demonstrated (FIG. 2c). Previous analysis of HCMV-infected neural precursor cells (NPCs) identified changes in levels of several human micro RNAs, including micro RNA 145 (miR-145), a negative regulator of Sox2 expression in human embryonic stem and glioma cells. Thus, efforts were taken to determine whether HCMV/IE1 regulation of Sox2 might occur via miR-145. To this end, a number of primary GBM tissues were screened for miR-145 and Sox2 levels by Taqman and western blot respectively. Using sequential RNA and protein extraction, it was demonstrated that HCMV infection of a GSC culture initially HCMV negative induced a 2.5 fold decrease in miR-145 concomitant with a ~2 fold increase in Sox2 protein (FIG. 2 d-e). Similar effects were measured in HCMV-infected NPCs. To demonstrate specificity, the assay was repeated in the presence of anti-miR-145 and found that HCMV-induced Sox2 and Oct4 levels and GSC tumor sphere growth, were partially inhibited by miR-145 knockdown (FIG. 2 f-i). It was considered possible that HCMV infection of GSCs inhibits miR-145 expression, which in turn relieves its negative regulation of Sox2 protein (FIG. 2j). Overexpression of HCMV IE1 gene in primary (HCMV negative) GSCs had a similar—albeit less profound—effect of inhibiting miR-145 and simultaneously up-regulating Sox2 protein, suggesting that other viral proteins downstream of IE1 might play a role in modulating this critical GSC regulatory network. Additionally, human NPCs transduced with IE1 exhibited increased levels of Bmi1 and EpCAM proteins, which regulate the survival of normal and cancerous stem cells.

Since Sox2 KD had been shown to inhibit GBM growth by regulating GSC proliferative and differentiation capacities, steps were taken to identify how IE1 KD modulates these processes in HCMV+GSCs. Using FACS and Affymetrix array profiling, it is demonstrated that IE1KD reduced the percentage of cells in S phase (11-24%) and significantly altered expression of multiple genes regulating glioma cell proliferation, including TOP2A and Ki-67. The effects of IE1KD on GSCs differentiation was also investigated using a seven day differentiation assay in conjunction with quantitative immunofluorescence analysis. IE1KD resulted in a significant reduction in the number of nestin positive (undifferentiated) cells, a rise in GFAP positive (astroglial) cells and no change in Tuj1 (neuronal-like) positive cells. These data suggest that IE1KD promoted GSCs differentiation toward astroglial lineage.

To more accurately assess both gain and loss of function associated with HCMV infection and IE1KD, primary GBM cells negative for HCMV were infected with HCMV and subjected to neurosphere assays in the presence of control or IE1siRNA. HCMV induced a significant increase in GSC growth, which was significantly inhibited by IE1KD (FIG. 3 a-d). Profound morphological changes of IE1KD GSCs (FIG. 3d) suggested activation of apoptosis-related pathways. Using apoptosis antibody arrays (FIG. 3e, the data show that IE1KD of HCMV-infected GSCs induced levels of pro-apoptotic proteins (Caspase 3, Bax, S15-p53) concomitantly with a decrease in anti-apoptotic protein levels (FIG. 3f-g,j). Late apoptosis was quantitatively assessed using a modified TUNEL assay, which demonstrated that IE1KD increased the percentage of apoptotic cells between 7-70% (FIG. 3h).

Figure 3I:
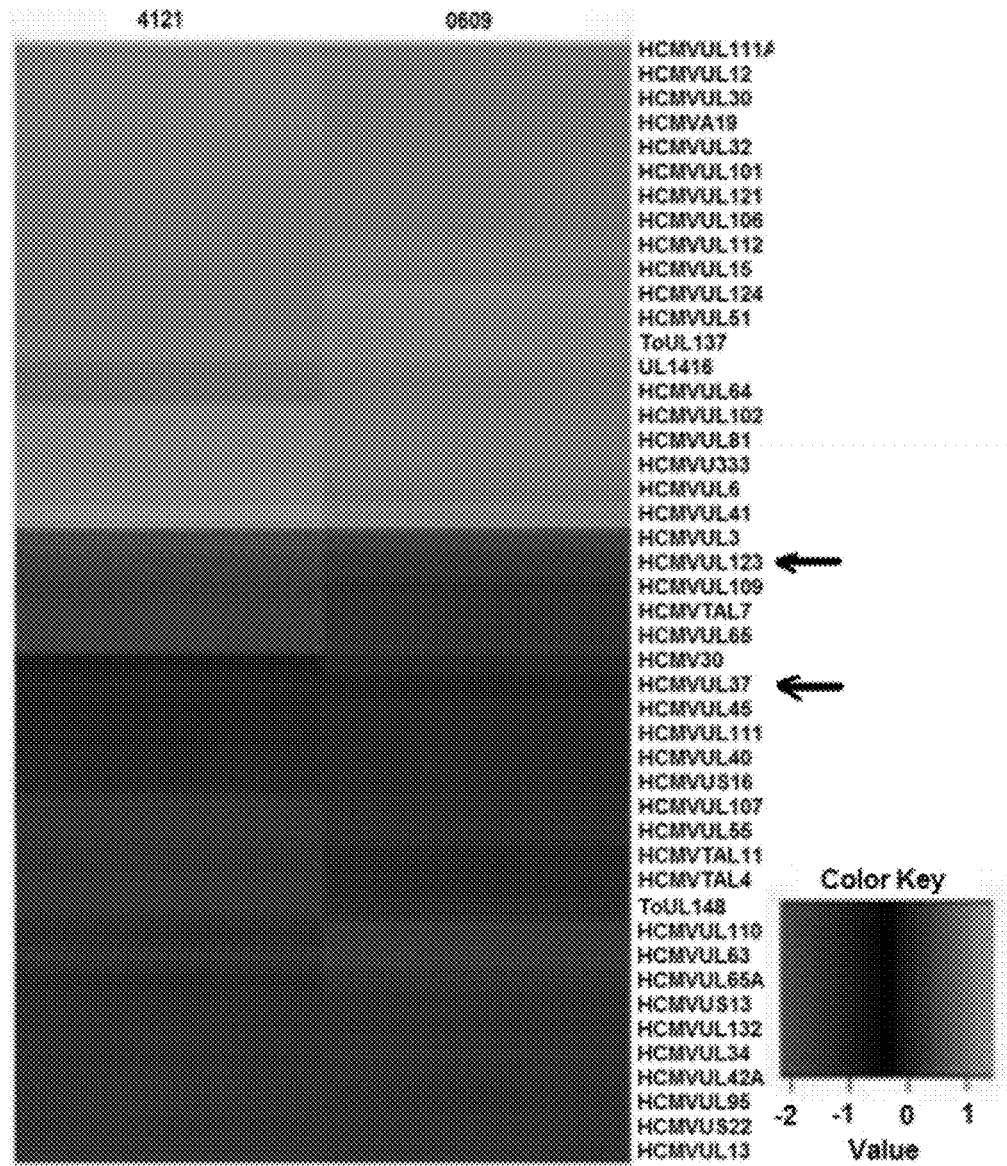

Since these cells were likely to express a larger repertoire of HCMV genes, experiments were performed to determine whether IE1KD inhibits expression of downstream viral transcripts involved in preventing cellular apoptosis. Using a HCMV DNA array to measure relative changes in transcript levels, a significant downregulation of HCMV UL123 (IE1) (FIG. 3i) and other viral transcripts, including HCMV UL37 (also known as viral mitochondrial inhibitor of apoptosis[25]), which negatively regulates expression of the pro-apoptotic cellular protein Bax, were identified. Western blot analyses confirmed inhibition of UL37 protein concomitant with increased Bax levels (FIG. 3i-j). These results indicate that in GSC whose growth is driven by HCMV, IE1KD induced cell death by unleashing multiple pro-apoptotic mechanisms.

Figure 4O:
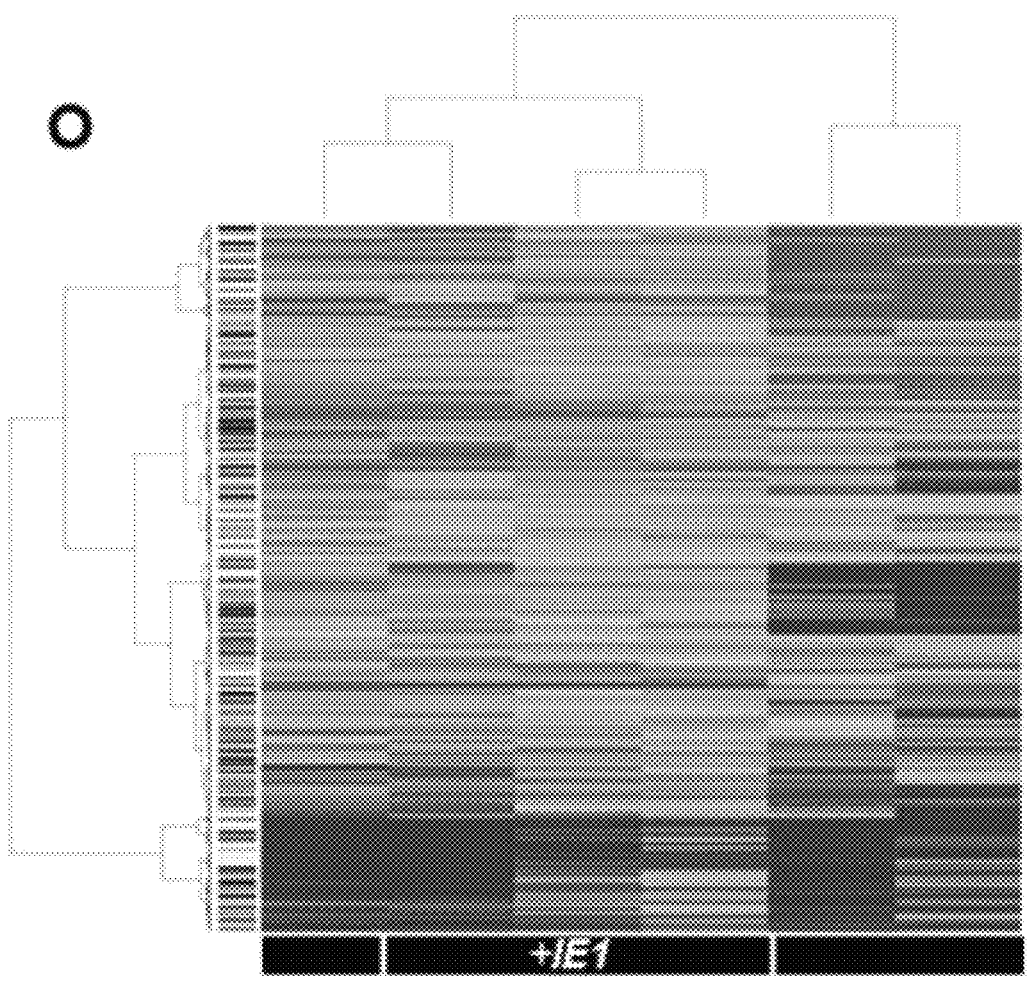
Figure 4P:
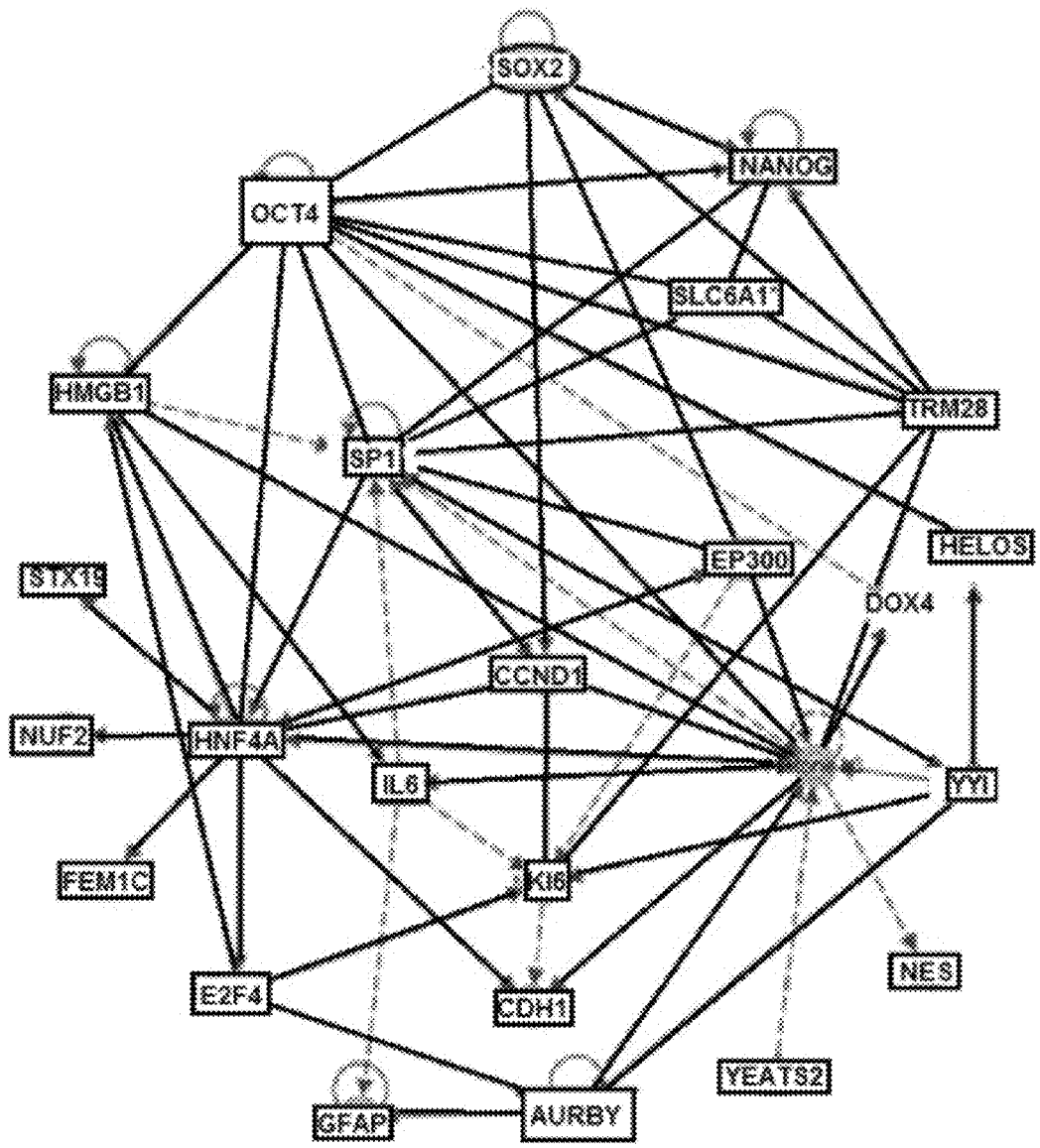

To directly investigate whether IE1 modulates glioma stem cells in vivo, a spontaneous mouse model of disease was used, which combines knockdown of the p53 tumor suppressor protein with overexpression of PDGF and N-RasV12 oncogenes in the developing neural stem cells. Twenty four neonatal mice (three repeat experiments/two groups each) were intra-cranially injected with different oncogene combinations+/−IE1, as described in Table 2. Tumor penetrance and grade distribution were similar across the two experimental groups (Table 2). Five weeks following oncogene administration, approximately 75% of mice developed high grade gliomas, exhibiting all pathognomonic features of the disease (Table 2). In addition, a "giant cell glioblastoma" phenotype was found in the IE1+ tumors. While expression of a single viral gene was unlikely to significantly impact survival, a mouse glioma model was used to interrogate markers of sternness and proliferation. Immunohistochemistry of matched IE1+/− glioma samples showed significant increase in levels of Sox2 and Nestin and decrease in GFAP levels in IE1+ tumors as compared to control tumors (FIG. 4a-n, s). Ki67, CD31, and p-STAT3 levels did not differ significantly between the two groups (FIG. 4a-b,s). As shown in FIG. 4o, IE1+ tumors clustered together in Affymetrix array analysis, revealing significant differences in expression of genes from several functional categories, including embryonic development, cell cycle, DNA repair, and cell death (FIG. 4p)—all cellular processes known to be "hijacked" by IE1 during HCMV infection. Immunohistochemical analyses confirmed that upregulation in transcript levels were paralleled by corresponding protein increases for Oct4 and Aurora B kinase, in the IE1+ gliomas (FIG. 4r-s). Interestingly, in human patients, p53 mutations cooperate with Aurora B kinase in driving giant cell glioblastoma, a phenotype uniquely associated with the IE1+ mouse gliomas. These data indicate that HCMV IE1 expression in the context of pre-existing genetic alterations significantly augmented the glioma stem-like phenotype in vivo.

TABLE 2

Histo-pathological Examination of Spontaneous Mouse Gliomas

| ouse | Oncogene Combination | Tumor/Grade | Ki67 | Sox2 | Nestin | GFAP | CD31 | Oct4 | IE1 | STAT3 | AurBK |
|---|---|---|---|---|---|---|---|---|---|---|---|
| 1 | *PDGF + Ras + p53KD | *II-III | | | | | | | | | |
| 2 | PDGF + Ras + p53KD | **IV | Y | Y | Y | Y | Y | Y | Y | Y | |
| 3 | PDGF + Ras + p53KD | *III | | | | | | | | | |
| 4 | PDGF + Ras + p53KD | **IV | Y | Y | Y | Y | | Y | Y | | Y |
| 5 | PDGF + Ras + p53KD + IE1 | ***IV | Y | Y | Y | Y | | Y | Y | | Y |
| 6 | PDGF + Ras + p53KD + IE1 | ^N | | | | | | | | | |
| 7 | PDGF + Ras + p53KD + IE1 | **IV | | | | | | | | | |
| 8 | PDGF + Ras + p53KD + IE1 | ***IV | | | | | | | | | |
| Exp 2 | | | | | | | | | | | |
| 9 | PDGF + Ras + p53KD | **IV | Y | Y | Y | Y | Y | Y | Y | Y | Y |
| 10 | PDGF + Ras + p53KD | ^N | | | | | | | | | |
| 11 | PDGF + Ras + p53KD | **IV | | | | | | | | | |
| 12 | PDGF + Ras + p53KD + IE1 | **IV | Y | Y | Y | Y | | | | | |
| 13 | PDGF + Ras + p53KD + IE1 | ***IV | | Y | Y | Y | Y | | Y | Y | Y |
| 14 | PDGF + Ras + p53KD + IE1 | ***IV | | Y | Y | Y | | Y | Y | | Y |
| Exp 3 | | | | | | | | | | | |
| 15 | PDGF + Ras + p53KD | ^N | | | | | | | | | |
| 16 | PDGF + Ras + p53KD | **IV | Y | Y | Y | Y | | | Y | | |
| 17 | PDGF + Ras + p53KD | **IV | Y | Y | Y | Y | | Y | Y | Y | |
| 18 | PDGF + Ras + p53KD | **IV | | | | | | | | | |
| 19 | PDGF + Ras + p53KD + IE1 | ^N | | | | | | | | | |
| 20 | PDGF + Ras + p53KD + IE1 | **IV | YY | Y | Y | Y | | | Y | | |
| 21 | PDGF + Ras + p53KD + IE1 | *III | | | | | | | | | |
| 22 | PDGF + Ras + p53KD + IE1 | ***IV | Y | Y | Y | Y | Y | Y | Y | Y | Y |
| 23 | PDGF + Ras + p53KD + IE1 | ***IV | Y | Y | Y | Y | Y | Y | Y | | Y |
| 24 | PDGF + Ras + p53KD + IE1 | ***IV | Y | | | | | Y | | | Y |
| Exp1-3 | IE1 + GBM = 77% | | | | | | | | | | |
| | IE1 − GBM = 62% | | | | | | | | | | |

*AA foci, frequent mitoses, minimal infiltration, no necrosis.
**Multifocal GBM with extensive sub-ependymal spread and brain invasion, frequent mitoses, microvascular proliferation, necrosis.
***Large GBM (or grade IV astrocytoma) with parenchymal invasion, necrosis, frequent mitosis and clusters of giant cells ("CMV like inclusion" or giant cell GBM).
^Organizing Hemorrhage, no tumour present.

HCMV impacts oncogenic signaling pathways at multiple levels, by activating receptor tyrosine kinases which drive gliomagenesis, such PDGFRα, by inducing an immunosuppressive environment, and by enhancing tumor-promoting "hubs", such as p-STAT3. The results provide insights into the role of HCMV/IE1 in regulating genetic and epigenetic networks that promote pluripotency, self-renewal, and growth of cancer stem cells and suggest that targeting IE1 in HCMV positive glioblastomas may have therapeutic benefits by selectively eliminating the cancer stem cell pool.

Example 2

US28

Cell Culture.

U251 and U87 cell lines were obtained from American Type Culture Collection (ATCC) and grown in DMEM/Ham's F-12+10% FBS. Primary glioblastoma/neural precursor cell-derived cultures were generated with tissue from surgical resections at the California Pacific Medical Center obtained according to the Institutional Review Board-approved protocol. Tissues were dissociated by enzymatic and mechanical dissociation. Single-cell suspensions were cultured with neural basal medium+N2 supplement, 20 ng/mL epidermal growth factor (EGF), 20 ng/mL basic fibroblast growth factor, and 1 µg/mL laminin. For ELISA for VEGF experiments and tube formation assays, cells were cultured in the absence of FBS or growth factors at least 48 hours prior to media collection. The NPC cell line was derived from the hippocampus tissue removed from a patient with intractable epilepsy. Cells were characterized by immunofluorescence and found positive for Nestin, GFAP, Tuj1, and Olig2. All experiments were carried out on passages 2 to 5 from the NPC culture. Human umbilical vein endothelial cells (HUVEC) were obtained from Invitrogen and grown in the complete endothelial cell growth media recommended by the manufacturer.

US28 Expression Vectors.

The Ad-US28 and Ad-Control adenoviruses were a gift from Dr. Dan Streblow, Oregon Health & Science University. The pcDEF-US28 plasmid was a gift from Dr. Martine Smit. The US28 insert was excised from the pcDEF plasmid and cloned into the pLXSN vector. Retroviruses were produced and used to infect glioma cells.

Viruses.

The Towne and AD169 HCMV strains were obtained from ATCC and grown in human embryonic fibroblasts. The TR virus strain was a gift from Dr. Lee Fortunato, University of Idaho (Moscow, Id.).

Knockdown Experiments Using siRNA to US28.

US28 knockdown was achieved with 2 siRNA oligonucleotide duplexes custom synthesized by Dharmacon. The sense sequences for the 2 siRNAs are as follows: CGACGGAGU-UUGACUACGAUU (SEQ ID NO:12) and CUCACAAA-UUACCGUAUU (SEQ ID NO:13). Experiments were carried out with each siRNA individually and the 2 duplexes were combined. As a negative control, nontargeting control pool from Dharmacon (D-001810-10-05) was used. Effective protein knockdown was verified at 48 and 72 hours posttransfection and prior to functional assays.

Fluorescence Measurements to Quantify US28 Expression Levels.

Images were taken at fixed exposure times with an Axio Image Z2 microscope (Zeiss). The fluorescence intensities, from at least 100 cells, were quantified with ImageJ software; plots representing cumulative distribution of mean pixel intensity for various conditions are shown. The Kolmogorov-Smirnov test was used to determine whether the measured differences were statistically significant.

Expression Profiling Using the HCMV DNA Array and the Affymetrix Gene ST1 Array.

Total RNA was isolated and the quality verified. The RNA was processed for microarray hybridization at the Center for Applied Genomics, UMDNJ-New Jersey Medical School. The HCMV arrays were printed and processed. Briefly, the array contains 65-mer oligonucleotides representing 194 predicted open reading frames (ORF) of the HCMV strain AD169, 19 oligonucleotides for ORFs in the Toledo strain that are not found in AD169, and 44 human genes as controls. Total RNA (3 µg) was reversed transcribed to cDNA using SuperScript II RT in the presence of cyanine-3 (Cy3) or cyanine-5 (Cy5) dUTP. The labeled cDNA was purified and hybridized to the arrays at 58° C. for 16 hours. The slides were scanned with an Axon 4200AL scanner, and the images were processed with GenePix Pro 6.1. A normalization factor was calculated using 36 human control genes (11) by dividing the median intensity of the Cy5 signal by the median intensity of Cy3 signal of the controls. The data were normalized by multiplying the Cy3 signal of each spot by the normalization factor. The ratio of the Cy5 median intensity to the Cy3 median intensity was determined for each spot and the average ratio determined for the replicate spots. The accession number for data from both Affymetrix and HCMV platforms is GSE31142.

HUVEC Tube Formation Assay.

Geltrex (Invitrogen #12760-013) was obtained from Invitrogen and thawed overnight at 4° C. One hundred microliters of Geltrex per well was placed on the bottom of 24-well culture dishes and allowed to solidify at 37° C. for 30 minutes. HUVECs were detached with EDTA and resuspended in endothelial cell medium supplemented with various growth factors or conditioned media at 40,000 cells/200 µL per well. Tubes were allowed to form for 8 to 10 hours, and cells were visualized with a Nikon Inverted Eclipse TE-2000E microscope, fitted with a CCD Cascade II camera. NIS Elements AR3.0 was used to acquire images, which were further processed in Photoshop.

Statistical Data Analysis.

Significant differences were determined by ANOVA or the unpaired Student t test, where suitable. Bonferroni-Dunn post hoc analyses were conducted when appropriate. The values of $P<0.05$ defined statistical significance.

Expression Profiling Using Affymetrix Arrays.

Affymetrix Human Gene 1.0 ST arrays were processed according to the Affymetrix Expression Analysis Whole Transcript (WT) Sense Target Labeling Protocol (Affymetrix Inc., Santa Clara, Calif.). Briefly, total RNA (300 ng) was converted to double strand cDNA. cRNA was obtained by an in vitro transcription reaction and used as the template for generating a new 1st strand cDNA. The cDNA was fragmented, end-labeled with biotin and hybridized to the Array for 16 hours at 45_C using the GeneChip Hybridization Oven 640. Washing and staining with Streptavidin-phycoerythrin was performed using the GeneChip Fluidics Station 450 and the images acquired using the Affymetrix Scanner 3000 7G Plus. The data was normalized using quantile normalization with the RMA algorithm (12) for gene-level intensities and the ratio determined for each gene using Partek Genomics Suite (Partek Inc St. Louis, Mo.). Total RNA was processed at the microarray facility from the center for applied genomics at Public Health Research Institute in New Jersey, using the Affymetrix Gene ST.1 Mean values of the 30 most up-regulated and 30 most down-regulated transcripts in the NPC_H-CMV vs. NPC_Untreated (control) are displayed using the R program heatmap.2 from the package 'gplots'. The package is available from the R repository CRAN, and is maintained by Gregory R. Warnes.

RT-PCR.

Brain tissue was homogenized and lysed in 1 mL QIAzol reagent (Qiagen) using a TissueRuptor homogenizer (Qiagen). RNA was then chloroform extracted and purified using the RNeasy lipid tissue mini kit (Qiagen). The quality of the RNA was verified by spectrometry and visualization of ribosomal RNA bands on an agarose gel. For each sample, 1 ug of total RNA was reverse transcribed using the iScript cDNA synthesis kit (BioRad) according to the manufacturer's instructions. Standard end-point PCR was then performed using the Taq PCR Core kit (Qiagen) with an input of 1 ug of cDNA for each experimental sample, water only for the negative control, and 1 ug of cDNA from CMV infected cells for the positive control. The primers used for PCR analysis are as follows: US28 F-5'-TCGCGCCACAAAGGTCG-CAT-3' (SEQ ID NO: 20), R-5'-GACGCGACACAC-CTCGTCGG-3' (SEQ ID NO:14); Rab14 F-GCAGATTTGGGATACAGCAGG-3' (SEQ ID NO:15), R-5'-CAGTGTTTGGATTGGTGAGATTC (SEQ ID NO: 16); UL56 F-5'-GTTGTTTCCCGAAAGTTTCATTAT-3' (SEQ ID NO:17), R-5'-CCTCTCTCACAATGTGGACATG-3' (SEQ ID NO:18). The PCR amplification cycle was repeated 50 times with a 60° C. annealing temperature for the US28 primers and a 58° C. annealing temperature for the Rab14 and UL56 primers. 20 uL of each 50 uL PCR reaction was resolved on a 1% agarose gel and the size of each amplicon (US28=390 base pairs, Rab14=167 base pairs, and UL56=249 base pairs) was verified relative to a 1 KB DNA ladder (Fermentas). The DNA from the remainder of each PCR reaction was then isolated using the MinElute PCR Purification kit (Qiagen) and sequenced.

Immunofluorescence and Immunohistochemistry.

Primary cultures and NPCs were fixed using methanol (10 min, RT) and immunostained using the following primary antibodies (overnight incubation, 4C): US28 C terminus, (sc#28042, 1/200), VEGF (sc#507, 1/200) from Santa Cruz Biotechnology, e-NOS from Abcam (Ab#5589, 1/1,000), COX2 (C4842, 1/500) from Cell Signaling, p-STAT3 (44380G, 1/500) and total STAT5 (44364G, 1/500) from Biosource. Fluorescently labeled secondary antibodies were from Invitrogen. For tissue immunohistochemistry, an antigen retrieval (Citra Plus, HK080-5K, from Biogenex) and pepsin digestion was used. Following overnight incubation with primary antibodies, Biogenex' supersensitive Polymer HRP IHC detection system was used following the manufacturer's directions (QD400-60K). Counterstaining was done using Hematoxylin. Cells and tissues were visualized using a Nikon Eclipse C1-Confocal microscope (Nikon TE2000-U) fitted with a "Cool Snap" Photometrix camera (Roper Scientific). Images were acquired using EZ-C1 v2.20 software and further processed using Photoshop (Adobe Photoshop CS4).

Human Phoshpho-Kinase Array and Western Blot Assays.

Cell lysates were prepared in the lysis buffer provided within the Proteome profiler array kit (catalog number ARY 003) from R&D. Parallel determination of the relative levels of protein phosphorylation was conducted according to the kit instructions, using 200_g protein/sample.

ELISA for VEGF was performed using the DUO ELISA KIT catalog #DY293B from R&D Systems, following manufacturer's instructions. Cells were serum starved (or grown in the absence of growth factors) for 48 h prior to collecting supernatants which were assayed for VEGF levels using the ELISA system described. ELISA for human CCL5 was performed using the R&D anti-human CCL5 neutralizing antibody (AB-278-NA, used a capture antibody) in conjunction with the recombinant human CCL5 and anti-CCL5-Biotinylated detection antibody, also from R&D (# BAF478).

Matrigel Invasion Assays.

Matrigel coated plates were obtained from BD Biosciences (BD catalog #354480) and used according to the manufacturer's instructions. Prior to invasion assays, cells were harvested using EDTA and resuspended in serum free media (0.1% BSA). 30,000 glioma cells/well were used in the case of U251 cells and 10,000 cells/well were used in the case of primary derived GBM cells. The lower chamber was filled with 200 ml complete growth medium. Where indicated, 50 ng/ml CCL5 (rhCCL5, catalog #278-RN/CF, from R&D) was added to the lower chamber. Cells were allowed to migrate into the Matrigel for 12 h after which, cells that remained in the Matrigel or attached to the upper side of the filter were removed with cotton tips following. Invasive cancer cells on the lower side of the filter were fixed and stained using Crystal violet. All invading cells were counted using an inverted microscope (10×). In neutralizing experiments, cells were preincubated with the anti-CCL5 antibody for 12 h prior to the invasion assay.

US28 protein expression in human glioblastomas was assessed by immunofluorescence analysis of primary glioblastoma-derived cultures and immunohistochemical analysis of paraffin-embedded tissues from several GBM specimens, including some that were used to generate the primary cultures. Reverse transcriptase PCR for US28, HCMV UL56 (a DNA packaging essential viral gene), and Rab14 (human housekeeping gene) was done using RNA isolated from snap-frozen tissues from the same cases. FIG. 5A shows an example of immunofluorescence analysis of primary GBM cells that exhibit cytoplasmic and membrane staining for the US28 antigen. Preincubation of the primary antibody with excess US28 blocking peptide showed specificity of immunostaining (FIG. 5B).

As shown in FIG. 5C, US28 expression was detected in paraffin-embedded GBM biopsy specimens. FIG. 5D shows specificity of staining, using the US28 blocking peptide in excess, as described earlier. Sections from the same sample show abundant staining for VEGF (FIG. 5E) and COX2 (FIG. 5F), suggesting the presence of enhanced angiogenesis and inflammation in and around the US28-positive tumor cells. The specificity of the US28 antibody was established by comparing immunostaining of cells that were mock-infected, HCMV-infected, or ectopically expressing US28. To confirm that HCMV US28 mRNA was likewise expressed in human GBM specimens, reverse transcriptase PCR on RNA extracted from GBM biopsy specimens from several different patients was performed. Uninfected NPCs showed no evidence of the amplified US28 gene product, or another conserved HCMV gene product UL56 (FIG. 5G). In contrast, amplified US28 RNA transcripts were detected in the primary GBM biopsy specimens from several patients, including a case found positive by immunohistochemistry (shown in FIG. 5C-F). All amplified US28 reverse transcriptase PCR products were sequenced to confirm specificity to HCMV, and unique gene polymorphisms were identified in several specimens, indicating that no cross-contamination of laboratory or PCR specimen occurred (C-terminal sequences alignment is provided in the Supplementary Information). Additional GBM and control brain tissues were immunostained for US28, COX2, VEGF, phospho-STAT3 (p-STAT3), and endothelial nitric oxide (e-NOS). Of the 35 different brain tissues screened, 53% were positive for US28 by reverse transcriptase PCR and 65% were positive by immunohistochemistry; there was more than 90% concordance in the results showing US28 detection when both approaches were used.

HCMV Infection of NPCs Induces Expression of US28 and CCL5, which Together Promote Glioma Invasiveness.

Figure 6A:
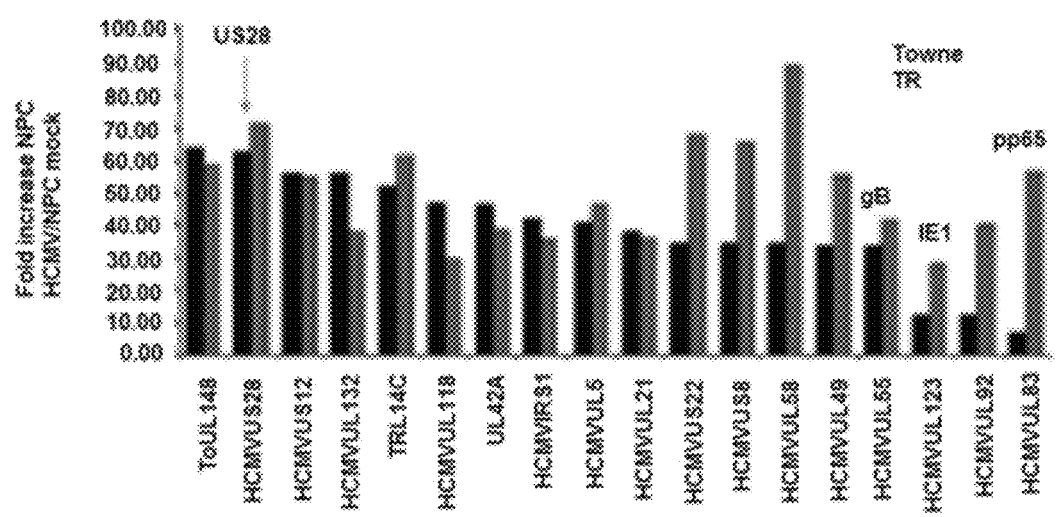
Figure 6B:
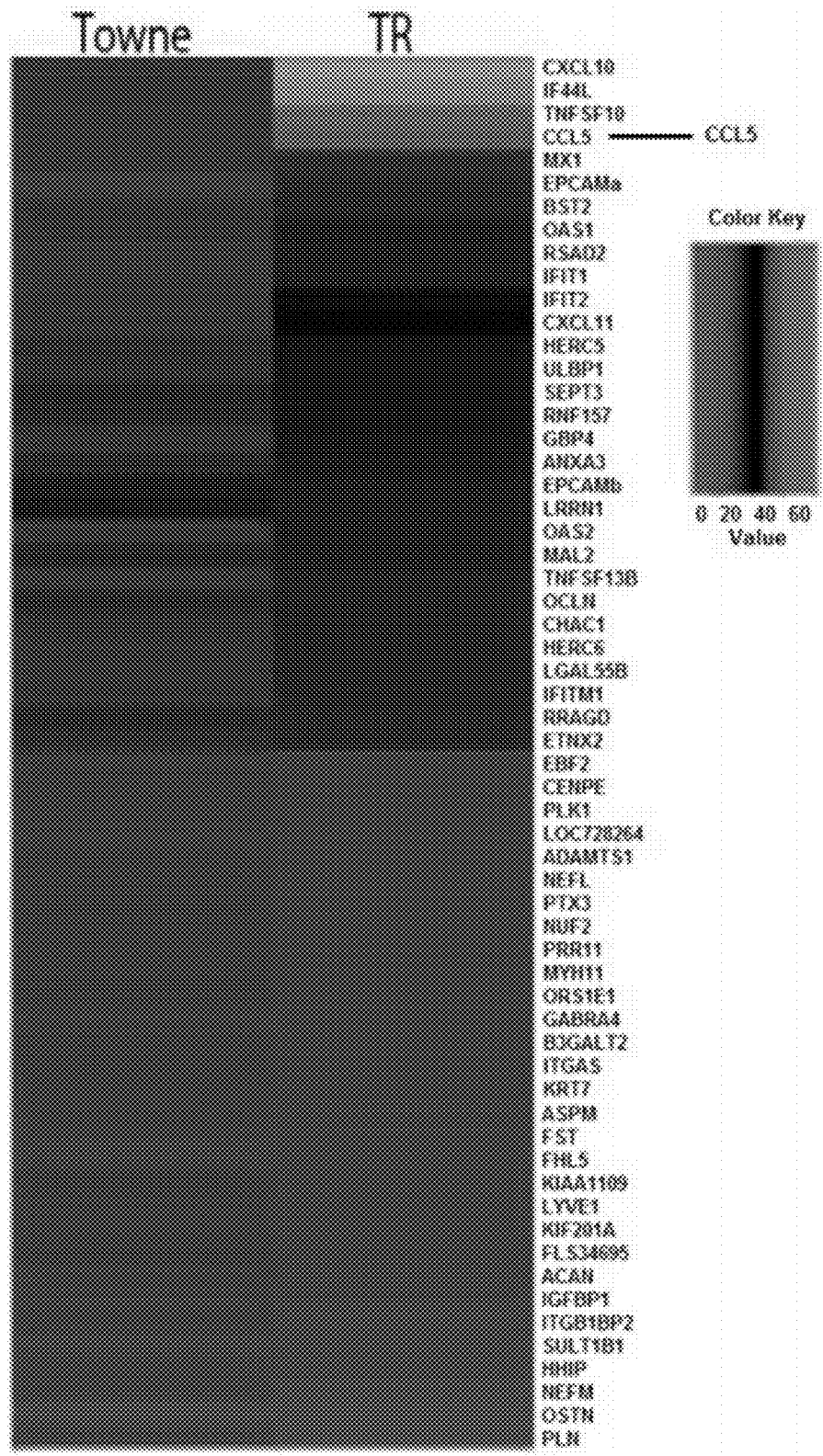

To understand the role HCMV US28 might play in gliomagenesis, steps were taken to ascertain whether US28 is expressed during HMCV infection of human adult NPCs, the purported cells of origin of adult GBM. NPCs were infected with HCMV [Towne and TR strains; multiplicity of infection (MOI)=1] or mock infected. Total RNA was harvested at 72 hours, and HCMV gene expression was assayed with a custom-made oligonucleotide microarray representing all the predicted ORFs for HCMV. The same samples were profiled with human Affymetrix DNA arrays. As shown in FIG. 6A, US28 was among the most abundantly expressed HCMV transcripts following infection with either viral strain. Interestingly, one of most upregulated human transcripts was the chemokine CCL5/RANTES (FIG. 6B, arrow). Although US28 can act as a constitutively active receptor, CCL5 is a bona fide ligand for US28 and can further stimulate US28 signaling, suggesting that US28 and CCL5/RANTES coexpression might induce a potent autocrine signaling loop. To determine whether expression of CCL5 is a relevant biomarker for GBM, the REMBRANDT GBM database was analyzed. It was determined that CCL5 expression levels were inversely correlated with survival in human glioblastomas (FIG. 6C). Analysis of previously characterized glioblastoma molecular subclasses showed that CCL5 expression levels are elevated in the "mesenchymal" GBMs, characterized by poor patient outcome.

To assess the effects of US28 expression on glioma invasiveness, a Matrigel invasion assays was performed comparing LXSN with US28-LXSN-transduced U251 and U87 glioma cells and 2 primary glioma cultures, which had no detectable HCMV transcripts. US28 overexpression resulted in an approximately 30% increase in the invasiveness of all glioma cell lines tested (FIG. 6D). The presence of 50 ng/mL recombinant human CCL5 in the bottom chamber further enhanced invasiveness of glioma cells and primary GBM cultures by 50% to 60%, as shown in FIG. 6D. These data show that CCL5, which is upregulated by HCMV infection, can augment US28-induced glioma cell invasion.

To establish the specificity of US28 effects on glioma cell invasion, an siRNA approach was used to knockdown US28 expression in a well-characterized human glioma cell line, U87, persistently infected with HCMV. US28 protein levels were measured by fluorescence intensity measurements of cells processed for US28 immunofluorescence. US28 siRNA1 induced an approximately 40% US28 knockdown, whereas siRNA2 induced approximately 60% US28 knockdown. When used together, siRNA1+2 induced approximately 80% US28 knockdown. A CCL5-neutralizing antibody was used to distinguish between US28 constitutive activity and the response to the CCL5 ligand secreted by human glioma cells. FIG. 6E shows that CCL5 levels were significantly (~75%) inhibited in U87 cells by preincubation with a CCL5-neutralizing antibody (20 ng/mL, 12 hours), regardless of the presence of HCMV or US28. Although US28 KD had no effect in uninfected U87 cells, Mat'rigel invasion of HCMV-positive U87 cells was inhibited by approximately 20% by US28 siRNA1 or 2 used alone and by 30% when the 2 siRNAs were used together (FIG. 6F). Pretreatment with CCL5-neutralizing antibody inhibited glioma cell invasion by approximately 30% to 35% and the use of both US28 knockdown and CCL5 neutralization did not further increase this effect (FIG. 6F). US28 knockdown a primary GBM culture, confirmed to be HCMV positive, resulted in inhibition of tumor cell invasion by approximately 35%; both baseline and in response to CCL5 stimulation.

US28 Activates Multiple Oncogenic Pathways in Human NPCs.

Figure 7D:
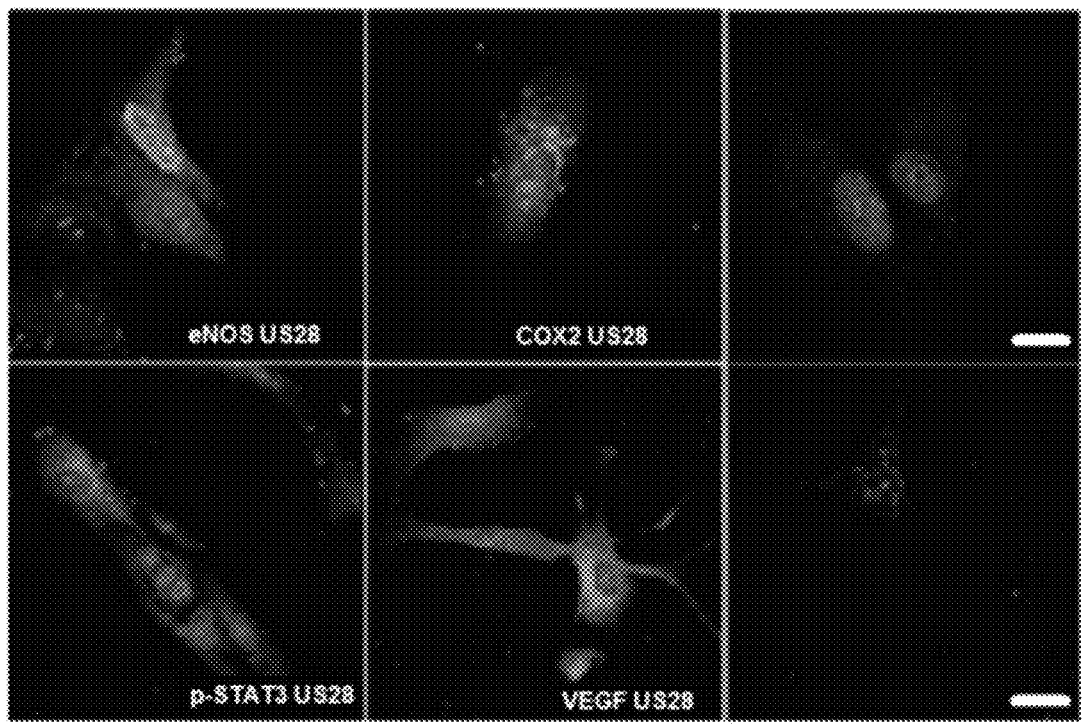

To determine additional oncogenic pathways activated by HCMV infection/US28 expression in NPCs, a phosphor-kinase human array (R&D Systems) embedded with antibodies specific for multiple phosphoproteins was used (FIGS. 7A and B). Pathways associated with glioma progression and invasion, including p-STAT3, AKT, ERK1/2, FAK, Src, and eNOS, were significantly activated by both whole virus infection and US28 overexpression in NPCs (FIG. 7C). Immunofluorescence analyses of US28 overexpressing NPCs confirmed upregulation of COX2, VEGF, p-STAT3, and e-NOS (FIG. 7D). e-NOS levels, which are elevated in gliomas, correlate with increased tumor aggressiveness. In addition to its proangiogenic role, e-NOS mediates production of nitric oxide, which was shown to induce the growth of glioma-initiating cells (16). This is the first report documenting that HCMV US28 induces e-NOS activation, which contributes to glioma pathogenesis.

Using Western blotting and immunofluorescence, it was confirmed that US28 induces p-STAT3 in neural precursor cells. STAT3 activation is critical for NPC malignant transformation toward a mesenchymal GBM phenotype, suggesting that US28-induced activation of p-STAT3 may contribute to gliomagenesis. Consistent with a recent report, US28 and p-STAT3 colocalize in primary glioblastomas in situ, which would explain why HCMV-positive glioma cells exhibit activation of the STAT3 pathway, implicated in promoting immunosuppression, maintenance of glioma stem cells, and tumor progression.

US28 Promotes GBM Angiogenesis.

Figure 8A:
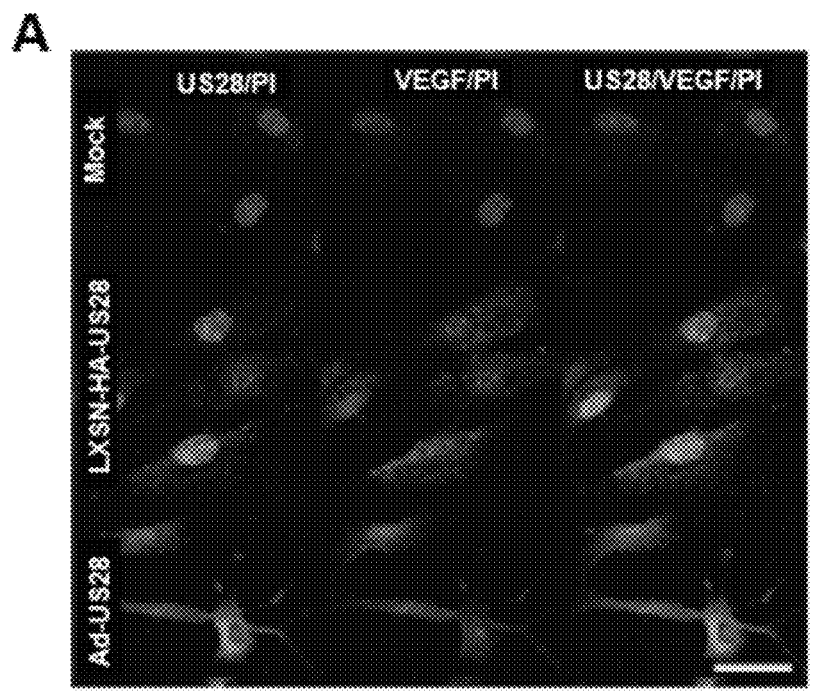

It was next determined whether US28 can modulate VEGF levels in neural precursor and glioma cells by immunofluorescence and ELISA. FIG. 8A shows that VEGF is significantly upregulated in US28-expressing NPCs. VEGF levels were measured in 4 different cell types (NPC, U251 and U87 glioma cell lines, and a primary GBM-derived line) by a highly sensitive ELISA. Seventy-two hours following infection with either Towne or TR HCMV strain, or US28 overexpression, VEGF was induced more than 2-fold in all cell types tested (FIG. 8B). US28 overexpression alone was sufficient to induce equivalent levels of VEGF expression to those found after whole HCMV infection, suggesting that US28 may play a predominant role in the HCMV-induced VEGF secretion. Remarkably, NPCs, which are nonmalignant, were also induced to produce VEGF, suggesting that US28 expression may promote an angiogenic phenotype in normal adult neural cells. An HUVEC tube formation assay was used to quantify angiogenesis. FIG. 8C shows that NPC HCMV-infected or overexpressing US28 produced supernatant enriched in proangiogenic growth factors that induced a dramatic increase in HUVEC tube formation compared with mock infection or transduction with control vector (FIG. 8D). These data indicate that US28 expression in a normal neural precursor cell could stimulate angiogenesis of neighboring endothelial cells. To show specificity of the US28 proangiogenic activity, loss-of-function experiments were performed, using siRNA to knock down US28 in persistently infected glioma lines, US28 knockdown inhibited VEGF production and glioma cell-mediated angiogenesis as measured by HUVEC tube formation assays. FIG. 9A illustrates US28 and VEGF detection in persistently infected U87 glioma cells before and after US28 knockdown. Quantification of immunofluorescence signals were used to measure the extent of US28 protein knockdown (FIG. 9B). Cumulative distribution of pixel intensity for immunopositivity illustrates that approximately 80% of US28-positive cells lost their signal after treatment with targeting US28 siRNA1+2, confirming effective protein knockdown (FIG. 9B). A similar level of US28 knockdown was achieved in the 4121-HCMV-infected cells following 72-hour treatment with targeting siRNA1+2. VEGF secretion was inhibited by US28 knockdown (FIG. 9B, bottom). Using ELISA, it was determined that VEGF levels (initially induced by HCMV) were inhibited by 35% in HCMV-infected U87 and primary glioma cells, following US28 knockdown using siRNA1+2 (FIG. 9C). Each US28 siRNA used separately had a more modest effect in inhibiting VEGF secretion, whereas uninfected glioma cells did not show a change in VEGF levels, confirming specificity of the US28 knockdown effect (FIG. 9C). Supernatants from persistently infected glioma cells with or without US28 siRNA1+2 were used in an HUVEC tube formation assay. As shown in FIGS. 9D and E, US28 knockdown significantly inhibited the proangiogenic activities of the HCMV-positive glioma cell supernatants. US28 knockdown in an endogenously infected primary GBM-derived culture inhibited VEGF secretion by approximately 50%, suggesting potential therapeutic benefits for targeting US28 in GBM patients.

Further analysis of primary GBM cells from patients identified several tumor cases in which US28 expression was significant and where VEGF expression had a high level of colocalization with US28 (FIG. 10A-C). Immunofluorescence analysis of primary GBM cells for eNOS and US28 indicated that US28 also colocalized with eNOS (FIG. 10D-F). Using paraffin-embedded tissue samples from the same patient, HMCV US28, VEGF, e-NOS, and COX2 were found to be coexpressed both in tumor cells and within the tumor microenvironment (FIG. 10G-L), suggesting that proinflammatory and proangiogenic signaling is, at least in part, initiated and promoted by US28 expression in infected GBM cells. Together with the other already described mechanisms, such as activation of the IL-6-p-STAT3 pathway, and induction of CCL5, HCMV US28 emerges as a key regulator of GBM progression by enhancing tumor cell invasion and angiogenesis (FIG. 10M).

Example 3 pp71

Protein extracts from GBM tissues were subjected to Western blot analysis using a pp71 antibody. Serum starved NPCs were transduced with recombinant adenoviruses expressing control protein (rAD-GFP) or viral protein HA-pp71 (rAD-pp71) for 48 hours. cDNA obtained from these samples was analyzed using the Oncogenes and Tumor Suppressor Genes PCR arrays (SA Biosciences). Control values were calculated for each gene and normalized relative to housekeeping genes (e.g., HPRT1, RPL13A, GAPDH). Fold change in expression of SCF and Myb are shown (KITLG also known as SCF, and MYB, underlined). Serum starved NPCs or U87 glioma cells were either untreated or transduced with rAD-GFP or rAD-pp71 for 48 hours. Supernataants were analyzed for secreted SCF using the human SCF DuoSet ELISA kit (R&D Systems). The same supernatants were used to treat HUVEC and tubular structures were allowed to form for 12 hours. The use of SCF neutralizing antibody demonstrates that pp71 specifically upregulates SCF.

What is claimed is:

1. A method of inhibiting the proliferation, growth and/or migration of a glioblastoma cell infected with cytomegalovirus in a subject comprising administering to the cell an inhibitor of a cytomegalovirus IE1 gene, comprising a duplex of inhibitory nucleic acids comprising SEQ ID NOS: 6 and 7, wherein the duplex of inhibitory nucleic acids inhibits the expression of the IE1 polypeptide encoded by the IE1 gene.

2. The method of claim 1 further comprising administering to the cell an inhibitor of cytomegalovirus US28 and/or an inhibitor of cytomegalovirus pp71, wherein the inhibitors of US28 and pp71 are inhibitory nucleic acids.

3. The method of claim 2 wherein the inhibitors of US28 and pp71 are siRNA or ribozyme molecules.

4. A method of treating a cell proliferative disease or disorder comprising exposing a cell infected with CMV and having aberrant cell proliferation to at least one siRNA that targets RNA encoded by a CMV IE1 gene, wherein the at least one siRNA is a double stranded RNA (dsRNA) molecule comprising a 3'dTdT and a 5' phosphate group, under conditions that permit induction of ribonucleic acid interference (RNAi), such that cell proliferation, growth and/or migration of the cell infected with CMV is inhibited and wherein the at least one siRNA comprises SEQ ID NOS:4 and 5, or SEQ ID NOS:6 and 7, or SEQ ID NOS: 4, 5, 6, and 7.

5. The method of claim 4, wherein the at least one siRNA comprises at least two siRNAs, each targeted to an RNA encoded by a different target gene.

6. The method of claim 4, wherein the at least one siRNA comprises three different siRNAs, each targeted to an RNA encoded by a different target gene.

7. The method of claim 5 or 6, wherein the target genes include one or both of cytomegalovirus US28 and pp71.

8. The method of claim 4, wherein the at least one siRNA is a double stranded RNA (dsRNA) molecule, each strand of which is about 18-29 nucleotides long.

* * * * *